US012727821B2

(12) United States Patent
Junker et al.

(10) Patent No.: US 12,727,821 B2
(45) Date of Patent: Sep. 8, 2026

(54) WEARABLE SENSORS FOR FALL DETECTION AND PREVENTION

(71) Applicant: MatrixCare, Inc., Bloomington, MN (US)

(72) Inventors: Ann Elizabeth Junker, Grafton, WI (US); Nate Sukhtipyaroge, Eagan, MN (US); Vivek Kumar, Eden Prairie, MN (US); Adhiraj Ganpat Prajapati, St. Paul, MN (US); Kedar Mangesh Kadam, Nova Scotia (CA); Keegan Duane Dsouza, Ocala, FL (US)

(73) Assignee: MatrixCare, Inc., Bloomington, MN (US)

( * ) Notice: Subject to any disclaimer, the term of this patent is extended or adjusted under 35 U.S.C. 154(b) by 732 days.

(21) Appl. No.: 18/055,916

(22) Filed: Nov. 16, 2022

(65) Prior Publication Data

US 2023/0148960 A1 May 18, 2023

Related U.S. Application Data

(60) Provisional application No. 63/362,077, filed on Mar. 29, 2022, provisional application No. 63/265,083, (Continued)

(51) Int. Cl.
*A61B 5/00* (2006.01)
*A61B 5/0205* (2006.01)
(Continued)

(52) U.S. Cl.
CPC .......... *A61B 5/6807* (2013.01); *A61B 5/0022* (2013.01); *A61B 5/0205* (2013.01);
(Continued)

(58) Field of Classification Search
CPC ... A61B 5/6807; A61B 5/0022; A61B 5/0205; A61B 5/1117; A61B 5/7264;
(Continued)

(56) References Cited

U.S. PATENT DOCUMENTS

2015/0020571 A1 1/2015 Chan et al.
2015/0112163 A1 4/2015 Wilmink
(Continued)

FOREIGN PATENT DOCUMENTS

KR 10-2019-0119879 A 10/2019
WO 2019/136110 A1 7/2019
WO 2021/161314 A1 8/2021

OTHER PUBLICATIONS

Bezold, J., Krell-Roesch, J., Eckert, T., Jekauc, D., & Woll, A. (2021). Sensor-based fall riskassessment in older adults with or without cognitive impairment: A systematic review. EuropeanReview of Aging and Physical Activity, 18(1). https://doi.org/10.1186/s11556-021-00266-w.
(Continued)

*Primary Examiner* — Adam J Eiseman
*Assistant Examiner* — Lucy Eppert
(74) *Attorney, Agent, or Firm* — Patterson + Sheridan, LLP

(57) ABSTRACT

Apparatuses and associated techniques for fall detection and prevention via wearable devices are provided. In one aspect, a wearable device is provided including one or more pressure sensors arranged on a bottom portion of the wearable device to collect pressure data from a bottom of a foot of a user, a wireless transmitter communicatively coupled with the one or more pressure sensors, and a power source coupled with the wireless transmitter.

20 Claims, 21 Drawing Sheets

Related U.S. Application Data filed on Dec. 7, 2021, provisional application No. 63/264,138, filed on Nov. 16, 2021.

(51) Int. Cl.
*A61B 5/11* (2006.01)
*G01L 5/00* (2006.01)
*G01L 5/16* (2020.01)
*G01P 15/14* (2013.01)

(52) U.S. Cl.
CPC .......... *A61B 5/1117* (2013.01); *A61B 5/7264* (2013.01); *A61B 5/7275* (2013.01); *G01L 5/0028* (2013.01); *G01L 5/16* (2013.01); *G01P 15/14* (2013.01); *A61B 2562/0219* (2013.01); *A61B 2562/0247* (2013.01)

(58) Field of Classification Search
CPC .......... A61B 5/7275; A61B 2562/0219; A61B 2562/0247; A61B 5/1036; A61B 5/002; A61B 5/1038; A61B 5/112; A61B 5/7267; A61B 5/6829; A61B 5/746; G01L 5/0028; G01L 5/16; G01L 1/146; G01L 1/205; G01P 15/14
See application file for complete search history.

(56) References Cited

U.S. PATENT DOCUMENTS

| | | | |
|---|---|---|---|
| 2015/0282766 A1 | 10/2015 | Cole et al. | |
| 2018/0228404 A1 | 8/2018 | Bhunia et al. | |
| 2019/0094088 A1* | 3/2019 | Reif | A61B 5/6807 |
| 2020/0155039 A1 | 5/2020 | Forth et al. | |
| 2020/0205746 A1* | 7/2020 | Burwinkel | G08B 21/0446 |
| 2020/0219372 A1 | 7/2020 | Kwatra et al. | |
| 2020/0237291 A1* | 7/2020 | Sundaram | A61B 5/4528 |
| 2022/0395229 A1* | 12/2022 | Everett | A61B 5/1038 |
| 2023/0000396 A1* | 1/2023 | Coffey | A61B 5/1117 |

OTHER PUBLICATIONS

Centers for Disease Control and Prevention. (Feb. 10, 2017). Important facts about falls. Centers for Disease Control and Prevention. Retrieved Oct. 17, 2021, from https://www.cdc.gov/homeandrecreationalsafety/falls/adultfalls.html.

Cho, H.-S., Yang, J.-H., Lee, J.-H., & Lee, J.-H. (2020). Evaluation of joint motion sensing efficiency according to the implementation method of SWCNT-coated fabric motion sensor. Sensors, 20(1), 284. https://doi.org/10.3390/s20010284.

Czech, M., Demanuele, C., Erb, M. K., Ramos, V., Zhang, H., Ho, B., & Patel, S. (2020). The impact of reducing the number of wearable devices on measuring gait in parkinson disease: Noninterventional exploratory study. JMIR Rehabilitation and Assistive Technologies, 7(2). https://doi.org/10.2196/17986. [Abstract Only].

Delahoz, Y., & Labrador, M. (2014). Survey on fall detection and fall prevention using wearable and external sensors. Sensors, 14(10), 19806-19842. https://doi.org/10.3390/s141019806.

Functional Gait Assessment. Shirley Ryan. (2016). Retrieved from https://www.sralab.org/rehabilitation-measures/functional-gait-assessment.

Gjoreski, M., Gjoreski, H., Lučtrek, M., & Gams, M. (2016). How accurately can your wrist device recognize daily activities and detect falls? Sensors, 16(6), 800. https://doi.org/10.3390/s16060800.

Habib, M., Mohktar, M., Kamaruzzaman, S., Lim, K., Pin, T., & Ibrahim, F. (2014). Smartphone-based solutions for Fall Detection and Prevention: Challenges and Open Issues. Sensors, 14(4), 7181-7208. https://doi.org/10.3390/s140407181.

Ho, C.-S., Chang, C.-H., Hsu, Y.-J., Tu, Y.-T., Li, F., Jhang, W.-L., Hsu, C.-W., & Huang, C.-C. (Jun. 1, 2020). Feasibility of the energy expenditure prediction for athletes and non-athletes from ankle-mounted accelerometer and heart rate monitor. Nature News. Retrieved Dec. 12, 2021, from https://www.nature.com/articles/s41598-020-65713-7.

Hua, A., Quicksall, Z., Di, C., Motl, R., LaCroix, A. Z., Schatz, B., & Buchner, D. M. (2018). Accelerometer-based predictive models of fall risk in older women: A pilot study. Npj Digital Medicine, 1(1). https://doi.org/10.1038/s41746-018-0033-5.

Huynh, Q. T., Nguyen, U. D., Irazabal, L. B., Ghassemian, N., & Tran, B. Q. (2015). Optimization of an accelerometer and gyroscope-based Fall Detection Algorithm. Journal of Sensors, 2015, 1-8. https://doi.org/10.1155/2015/452078.

Khandanpour, N., Armon, M. P., Jennings, B., Clark, A., & Meyer, F. J. (2009). Photoplethysmography, an easy and accurate method for measuring ankle brachial pressure index: Can photoplethysmography replace Doppler? Vascular and Endovascular Surgery, 43(6), 578-582. https://doi.org/10.1177/1538574409334829. [Abstract Only].

McDermott, A. (Dec. 22, 2016). Why are people ticklish? Healthline. Retrieved Dec. 2, 2021, from https://www.healthline.com/health/why-are-people-ticklish.

OVPRI. Examples of Potential Risks to Subjects. (n.d.). Retrieved Dec. 2, 2021, from https://research.uoregon.edu/manage/research-integrity-compliance/human-subjects-research/examples-potential-risks-subjects.

Stages of Parkinson's. Parkinson's Foundation. (n.d.). Retrieved Nov. 30, 2021, from https://www.parkinson.org/Understanding-Parkinsons/What-is-Parkinsons/Stages-of-Parkinsons.

University of Missouri, School of Health Professions, Department of Physical Therapy. (2005). Global Deterioration Scale. Geriatric Examination Tool Kit. Retrieved from https://geriatrictoolkit.missouri.edu/cog/Global-Deterioration-Scale.pdf.

Wisconsin Parkinson Association. (Nov. 24, 2021). Retrieved Dec. 2, 2021, from https://www.wiparkinson.org/.

K. Toda and N. Shinomiya, "Machine learning-based fall detection system for the elderly using passive RFID sensor tags," 2019 13th International Conference on Sensing Technology (ICST), Sydney, NSW, Australia, 2019, pp. 1-6, doi: 10.1109/ICST46873.2019.9047732. [Abstract Only].

Mansfield et al., "Objective Pressure Injury Risk Assessment Using a Wearable Pressure Sensor," IEEE International Conference on Bioinformatics and Biomedicine (BIBM), 2019, pp. 1-8.

PCT, Notification of Transmittal of the International Search Report and the Written Opinion of the International Searching Authority, or the Declaration for Application PCT/US2022/079961 dated Feb. 16, 2023.

International Preliminary Report on Patentability received for PCT Patent Application No. PCT/US2022/079961, mailed on May 30, 2024, 10 pages.

Forbes et al., "Fall prediction using behavioural modelling from sensor data in smart homes", Artificial Intelligence Review, vol. 53, No. 2, Mar. 16, 2019, pp. 1071-1091.

Supplementary European Search Report and Search Opinion Received for EP Application No. 22896686.7, mailed on Sep. 8, 2025, 9 pages.

* cited by examiner

WEARABLE SENSORS FOR FALL DETECTION AND PREVENTION

CROSS-REFERENCE TO RELATED APPLICATIONS

This application claims benefit of U.S. provisional patent application Ser. No. 63/264,138 filed Nov. 16, 2021, U.S. provisional patent application Ser. No. 63/265,083 filed Dec. 7, 2021, and U.S. provisional patent application Ser. No. 63/362,077 filed Mar. 29, 2022. The aforementioned related patent applications are herein incorporated by reference in their entirety.

BACKGROUND

Field

Embodiments of the present disclosure relate to wearable devices. More specifically, embodiments of the present disclosure relate to using wearable devices to detect and prevent falls.

Description of the Related Art

In a wide variety of medical (and non-medical) settings, users falling down (e.g., from standing, seated, or walking positions) are among the most common, as well as most dangerous, risks. This is particularly true among those with reduced mobility due to, for example, age, physical condition, injury, and the like. Conventionally, fall prevention involves generic and simplistic solutions such as use of a cane, installation of handrails, and potentially physical therapy to improve strength. However, these approaches fail to account for a wide variety of practical issues, and do not provide adequate or complete solutions. Further, they do not enable targeted prediction of fall risks and particularized intervention.

SUMMARY

According to some embodiments of the present disclosure, a smart sock is provided. The smart sock includes one or more pressure sensors arranged on a bottom portion of the smart sock to collect pressure data from a bottom of a foot of a user; a wireless transmitter communicatively coupled with the one or more pressure sensors; and a power source coupled with the wireless transmitter.

According to some embodiments of the present disclosure, a wearable device is provided. The wearable device includes one or more pressure sensors arranged on a bottom portion of the wearable device to collect pressure data from a bottom of the foot of the user; one or more ankle sensors arranged on an ankle portion of the wearable device; a wireless transmitter communicatively coupled with the one or more pressure sensors and the one or more ankle sensors; and a power source coupled with the wireless transmitter.

According to some embodiments of the present disclosure, a method is provided. The method includes receiving, from a wearable device on a foot of a user, pressure data for a bottom of the foot of the user; receiving, from the wearable device, ankle sensor data from one or more ankle sensors arranged on an ankle portion of the wearable device; predicting a fall of the user based on the pressure data and the ankle sensor data; and initiating one or more interventions based on the predicted fall.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

Figure 1A:
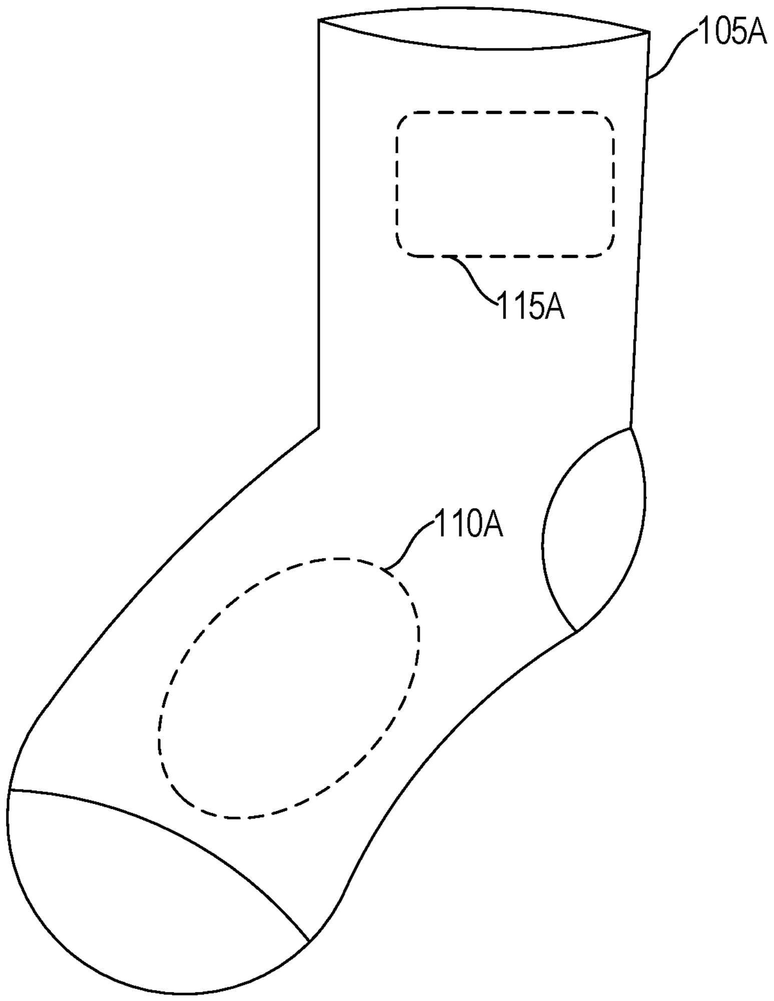
FIG. 1A depicts an example wearable device for improved fall detection and prediction.

Additional aspects of the present disclosure can be found in the attached appendix.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Aspects of the present disclosure provide apparatuses and associated methods, processing systems, and computer-readable mediums for improved detection and prevention of user falls.

Embodiments of the present disclosure provide wearable devices, to be worn on the foot of the user, to enable improved and streamlined data collection via a variety of sensors. In embodiments, the sensor data from such wearable devices can be evaluated and analyzed using a variety of systems, including rules-based approaches and machine learning-based approaches, to detect and/or predict (and, in some embodiments, prevent) user falls. In some embodiments, the wearable device can include one or more pressure sensors arranged to collect pressure data for one or more points or areas on the bottom of the user's foot. In some embodiments, the wearable device can additionally or alternatively include one or more ankle sensors arranged on or near the user's ankle. Such ankle sensors may include, for example, one or more accelerometers, one or more inertial sensors, one or more gyroscopes, one or more blood pressure or pulse rate sensors, and the like. In some embodiments, the wearable device is a smart sock (e.g. with one or more sensors integrated into the sock, or removably attached to the sock). In other embodiments, the wearable device may be other items such as a smart shoe.

In some embodiments, the sensor data indicates pressures at one or more positions on a user's feet can be collected and evaluated using one or more trained machine learning models to predict the likelihood of a future fall and/or the potential severity of such a fall. As used herein, pressure data from the "user's feet" is generally inclusive of pressure on the user's actual feet, pressure on leg or foot prosthetics of the user, and the like. In some aspects, pressure data on the user's feet can also include the pressure distributions on assistive devices used by the user, such as a cane, walker, and the like.

As used herein, the fall risk (also referred to as risk of a fall) may generally refer to the likelihood or probability of such a fall in the future, the potential severity of such a fall, or a combination of the likelihood and severity. A number of preventative and/or remedial actions can be initiated based on this analysis.

In some embodiments, the sensor data is collected via one or more wearable devices, as discussed above. For example, the pressure data may be collected via insoles in the user's shoes, where the insoles are configured with one or more sensors (e.g., pressure sensors) to detect pressure exerted by the user's foot in one or more locations on the foot, via smart shoes themselves, via smart socks, and the like. By using this pressure data, the system is able to perform a balance assessment (e.g., using the pressure on each portion of each insole). Although pressure data is used in various examples discussed herein, in some embodiments, other sensor data (such as accelerometer data, inertial sensor data, and the like) can similarly be collected for the user(s).

For example, in some embodiments, the other sensor data can include ankle data from one or more sensors on the ankle of the user. In one such embodiment, the sensor data may include data from one or more accelerometers on each foot of the user, one or more gyroscopes, and the like. Such data may be beneficial in improving the detection and prevention of falls, as compared to evaluating solely pressure data. For example, such ankle sensors enable understanding of not only how pressure is distributed when the foot is placed on the ground, but also how the foot and leg are moved (e.g., the angles or orientations of the foot at each point in the walk cycle), how quickly they are moved, how the ankle is rotated during the walking cycle, and the like.

As used herein, the sensor data can generally include any data collected from wearable devices on or near the user's foot, including pressure data from the bottom of the foot, blood pressure data collected via a sensor on or near the ankle of the user (e.g., arranged on the inside of the ankle, just above or immediately proximal to the malleolus), pulse rate and/or oxygen saturation of the user (e.g., via a sensor similarly placed above or near the malleolus), motion data from one or both feet (e.g., collected via accelerometers arranged on the ankle of the user), orientation data from one or more both feet (e.g., collected using gyroscopes on the ankle), and the like.

In at least one embodiment, falls can be detected or identified based on evaluating this collection of sensor data. For example, detecting a reduced or eliminated pressure on the bottom of the foot, coupled with a determination that the user orientation has changed (e.g., using the gyroscopes) and a rapid speed of the change (e.g., above a threshold, as determined using accelerometers), the system may determine that the user has fallen, and therefore generate interventions such as alerts, warnings, instructions to caregivers, and the like. In some embodiments, falls can similarly be predicted based on such rules-based systems or machine learning-based systems by evaluating the sensor data, enabling improved and advance warning.

In at least one embodiment, the pressure data is collected via one or more pressure sensors or plates that are integrated into the wearable device (e.g., sewn into a smart sock), while the ankle data (e.g., blood pressure data, gyroscope data, motion data, and the like) can be collected via one or more components that are detachably or removably attached to the ankle of the user. For example, an accelerometer and gyroscope may be included within a sensor unit that can be attached to the ankle of a smart sock, such as by inserting it into a pocket sewn into the sock, attaching it to the sock using a hook and loop system, and the like. In one such embodiment, a power source and/or wireless transmitter and/or receiver may also be included in such a removable unit, allowing potentially sensitive components to be easily removed (e.g., to wash the smart sock, to charge the unit, and the like).

In some embodiments, the sensor data can be monitored as the user walks and otherwise moves (e.g., in their normal environment, in the shoes they normally wear, and the like). Generally, this sensor data can be used in a variety of computational systems, including to predict and/or prevent falls, to inform or improve treatment options (e.g., to suggest improved physical therapy options), and the like. In some aspects of the present disclosure, residential care facilities are used as example locations where users (e.g., residents) may use the wearable devices described herein. However, embodiments of the present disclosure are readily applicable to a wide variety of locales, including both within medical or residential facilities (such as hospitals or nursing homes) as well as in any general environment (e.g., within private domiciles, in public spaces such as shopping centers or parks, and the like).

In some embodiments, the system evaluates sensor data at discrete instances in time. In other embodiments, the system evaluates the sensor data over windows of time to analyze motion or walking patterns of the user. For example, the system may evaluate the data to determine whether the user is walking normally on one foot while dragging the other somewhat or moving one through unusual or awkward angles (which may indicate an increased risk of fall).

In some embodiments, the data is evaluated using one or more machine learning (ML) and/or artificial intelligence (AI) models. These models may enable the system to determine what sensor data is normal and/or acceptable, and what may trigger further concerns.

In some embodiments, in addition to or instead of evaluating the data to predict the potential for a fall, the system uses models to predict the fall severity of such a fall. For example, if the user falls forwards, they may be likely to suffer reduced harm, as compared to falling backwards. In some embodiments, the particular sensor data may be used by trained models to predict this severity. In some embodiments, therefore, the sensor data may be used to predict which direction the user will fall. In some embodiments, the potential results are also determined or generated (e.g., head trauma from falling backwards, broken wrist from falling forwards, broken hip from falling sideways, and the like).

In some embodiments, to train these models, the system uses labeled training data collected from one or more users while the users are engaging in ordinary activities (e.g., walking). In one such embodiment, data is collected from a group of users over time, and each time a fall occurs or is reported, the sensor data from the fallen user may be labeled as preceding a fall. For example, the system may automatically label the previous N minutes of data as imminently preceding a fall, and/or label the previous M days of data to indicate that a fall followed some days later. In some embodiments, the system further labels the data based on the characteristics of the fall, such as the fall direction, fall severity, and the like.

In at least one embodiment, in addition to sensor data, the training data can further indicate various characteristics of the user, such as their age, gender, weight, height, any mobility restrictions, whether the user uses any assistive devices such as a can or walker, and the like. By including such characteristics in the input to the models, the system may be able to generate more accurate fall predictions, as discussed in more detail below.

In embodiments, this training data can be used to train one or more machine learning models to predict falls (either imminent falls or potential future falls), to predict the severity of such a fall, and the like.

In embodiments, the sensor data can be used to predict a future fall for a given user even if the given user has not suffered a recorded fall in the past. For example, the machine learning model(s) may be trained using sensor data from a variety of users (some of whom may have fallen before, during, or after the sensor data was collected). These models can thereby learn to recognize patterns of sensor data (e.g., blood pressure data, ankle orientation data, pressure data, and the like) that tends to precede such falls. These models can thereafter be used to evaluate sensor data for specific users to predict whether the user is likely to fall in the future, regardless of whether the user has fallen in the past. For example, in some embodiments, sensor data such as the user's blood pressure, heart rate, and changes in walking patterns (e.g., changes from a benchmark or previous pattern of the user) can be used as predictors for future falls of the user.

In embodiments, these predictions can be used to drive a wide variety of patient-specific interventions. For example, the system may respond to an immediate risk by dispatching aid (e.g., alerting a nearby caregiver), instructing the user to stop, sit, or otherwise rest, and the like. In some embodiments, the system can additionally or alternatively initiate various preventative actions, such as modifying physical therapy plans (e.g., to strengthen the muscles of the patient that will help to prevent the particular type of fall that is predicted), assigning or providing assistive devices such as a cane or walker, and the like.

In some embodiments, the sensor data includes multiple individual pressure points on each foot of each user. For example, the system may receive and evaluate, for each foot, two points on the ball of the foot (e.g., the pressure at the front-left point of the foot and the front-right point of the foot) one or more points on the heel of the foot (e.g., at the rear-center of the foot), and the like.

In some embodiments, in addition to or instead of predicting falls, the models can be used for diagnostic purposes, such as to detect when a user is putting extra pressure on one side, moving one or both feet through unusual or inappropriate orientations or speeds while walking, or generally favoring or disfavoring one side (which may indicate pain or other issues on the other side).

Further, in some embodiments, the models can be used to not only predict imminent falls (e.g., falls that may occur in the next few seconds, minutes, or days), but also to evaluate more long-term trends (e.g., to determine whether the user is losing their balance or wavering more frequently now than they did before, even in the absence of an actual fall).

In at least one embodiment, the predictive models can also be used to identify and remediate potential hazards in the physical space, such as rugs, uneven floors, cords across the walkway, and the like. For example, the system may identify region(s) in a facility where fall events are more common, where near-fall events occur (e.g., detected stumbling, wavering, or tripping), where predicted falls are often flagged, and the like. In some embodiments, the system can generate a heat map for the facility, indicating the average fall risk and/or predicted severity across the floorplan, and across a number of users and/or times. By evaluating this data, the system can identify potential hazards that are causing (or may cause) falls, and thereby initiate remediation that can prevent such occurrences.

In some embodiments of the present disclosure, the smart wearable devices (e.g., smart socks) can additionally or alternatively be used to evaluate and monitor the progression of user diseases, such as Parkinson's disease. For example, the wearable devices may be used to benchmark the user's current status (e.g., current or average walking patterns, blood pressure patterns, and the like) against their earlier data (e.g., prior or historical walking patterns) and/or later data (e.g., walking patterns recorded or determined subsequently). By identifying changes in such patterns, the system may track disease progression and user state. In some embodiments, the wearable devices can similarly be used to monitor user progress during various interventions such as physical therapy. For example, by comparing current and past sensor data, the system can enable evaluation of how well the therapy is working for the specific user as an intervention (e.g., how much the walking patterns have improved, how quickly they improved, and the like).

Example Wearable Device for Improved Fall Detection and Prevention

FIG. 1A depicts an example wearable device 105A for improved fall detection and prediction.

In the illustrated example, the wearable device 105A comprises a sock (e.g., a garment for the foot and/or lower part of the leg of the user). In some embodiments, the wearable device 105A can have a style, thickness, material, and other design to closely mirror common or preferred socks of the user(s), such that the wearable device 105A feels more akin to an ordinary sock, rather than a smart device. For example, the wearable device 105A may be a medium-weight crew-style sock, made using a nylon-cotton blend of material. In some embodiments, multiple types and styles of wearable device 105A may be available, allowing each individual user to select the type and material that is most comfortable or typical for them.

Advantageously, as the wearable device 105A can be designed and customized to the specific preferences of the user in some embodiments, the collected sensor data can be more accurate and reliable. For example, users are generally more likely to consistently use the wearable device 105A if it feels unobtrusive and comfortable, allowing the system to collect more consistent data for the user. Similarly, if the wearable device 105A is comfortable and unobtrusive, the resulting sensor data may be more reflective of the actual walking patterns of the user (e.g., because the user is less likely to walk awkwardly or differently simply due to the presence of the wearable device 105A).

In the illustrated embodiment, the wearable device 105A includes two discrete sensor areas, including one or more pressure sensors 110A on the base or bottom of the sock (thereby arranged to collect data from the bottom of the user's foot), as well as one or more ankle sensors 115A located on or near the ankle portion of the wearable device 105A (thereby arranged to collect data from on the ankle of the user). In some embodiments, the wearable device 105A may include only the pressure sensors 110A, only the ankle sensors 115A, or both.

In some embodiments, as discussed above and below in more detail, the pressure sensors 110A can generally include one or more components that are configured to detect pressure (and indicate the amount of pressure), such as a pressure transducer that converts input mechanical pressure into an electrical output signal indicating the amount of pressure. In embodiments, the pressure sensor 110A can include a wide variety of sensor types, including strain gauge-based instruments (e.g., where a flexible element such as a thin metal strip or a film can be moved by the mechanical pressure, allowing for measurement of the pressure), capacitive sensors (e.g., where a diaphragm and/or pressure cavity is used to define a variable capacitor, where mechanical pressure can change the size of the cavity and thereby change the measured capacitance), a piezo-resistive sensor, and the like.

In at least one embodiment, the pressure sensor(s) 110A are integrated into the wearable device 105A, such that they are unobtrusive or imperceptible to the user. For example, the pressure sensors 110A may be thin components (e.g., thinner than a defined maximum depth, which may be determined based on user preference or experimentation) sewn into or otherwise included in the wearable device 105A.

In some embodiments, the pressure sensors 110A may be powered and/or controlled locally. That is, the power source (if needed), communication systems (e.g., to transmit the pressure data to one or more other components), and the like may be included in the pressure sensors 110A themselves. In other embodiments, as discussed below in more detail, such components may be included on or with the ankle sensors 115A. In one such embodiment, one or more wires, cables, or other communication links may be provided to connect the pressure sensors 110A to the relevant other components (e.g., to a power source and wireless transmitter).

In the illustrated embodiment, the ankle sensors 115A are arranged on the ankle portion of the wearable device 105A, such that they will be proximate to the ankle of the user when the wearable device 105A is worn. In some embodiments, the ankle sensors 115A are included on the inner side of the user's ankle (e.g., on the medial side of the ankle or foot). In embodiments, the ankle sensors 115A can generally include a wide variety of sensors, such as gyroscopes, accelerometers, inertial sensors, blood pressure sensors, heart rate or pulse sensors, blood oxygen sensors, and the like.

In some embodiments, the ankle sensors 115A are integrated into the wearable device 105A in a similar manner to the pressure sensors 110A (e.g., sewn into the fabric of the sock). In some embodiments, some or all of the ankle sensors 115A are included within one or more removable components. For example, the ankle sensors 115A may be enclosed within a sensor housing that is removably attached to the wearable device 105A, such as by inserting it into a sewn pocket, attaching it with a stretchable band, and the like. In some embodiments, the removable component can generally include any elements that are not washable or are otherwise sensitive. For example, if a given sensor (such as an accelerometer) can be safely washed (either by hand or in a washing machine), the given sensor may be integrated into the wearable device 105A. Other sensors or components which are not washable (e.g., blood pressure sensors, power sources, and the like) may be included in a removable component.

In some embodiments, as discussed above, the area of the ankle sensors 115A can also include any other needed components, such as a transmitter, a power source (e.g., a rechargeable or replaceable battery), and the like. In at least one embodiment, the ankle sensors 115A (or the unit or component including them) is a slim-line component (e.g., less than a defined maximum thickness) that renders it unobtrusive for the user (e.g., such that it does not interfere with ordinary walking).

In some embodiments, as discussed above, the ankle sensors 115A (or accompanying components such as power source and transmitter) may be communicatively coupled with the pressure sensors 110A. This communication link may include wireless connectivity (e.g., via a short-range radio communication), wired connectivity (e.g., via one or more wires or cables connecting the pressure sensors 110A to the ankle sensors 115A and/or other components), and the like.

Example Wearable Device for Improved Fall Detection and Prevention

Figure 1B:
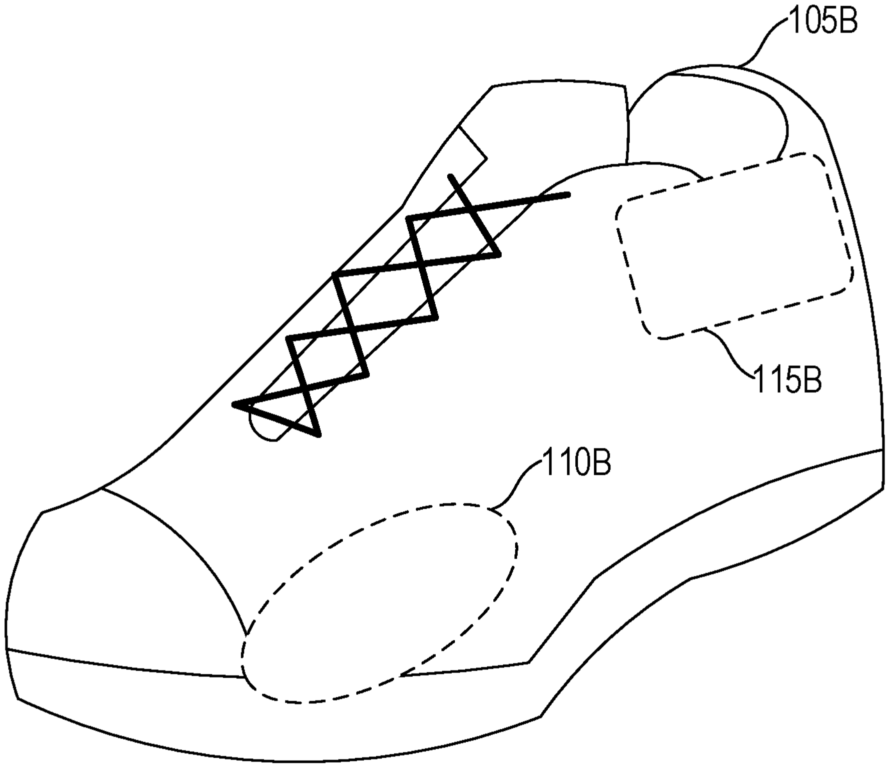
FIG. 1B depicts an example wearable device for improved fall detection and prediction.

FIG. 1B depicts an example wearable device 105B for improved fall detection and prediction.

In the illustrated example, the wearable device 105B comprises a shoe. In some embodiments, the wearable device 105B can have a style, thickness, material, and other design to closely mirror common or preferred shoes of the user(s), such that the wearable device 105B feels more akin to an ordinary show, rather than a smart device. For example, the wearable device 105B may be a running or walking shoe, a slipper, a boot, and the like. In some embodiments, multiple types and styles of wearable device

105BA may be available, allowing each individual user to select the type and material that is most comfortable or typical for them.

Advantageously, as the wearable device 105B can be designed and customized to the specific preferences of the user in some embodiments, the collected sensor data can be more accurate and reliable. For example, users are generally more likely to consistently use the wearable device 105B if it feels unobtrusive and comfortable, allowing the system to collect more consistent data for the user. Similarly, if the wearable device 105B is comfortable and unobtrusive, the resulting sensor data may be more reflective of the actual walking patterns of the user (e.g., because the user is less likely to walk awkwardly or differently simply due to the presence of the wearable device 105B).

In the illustrated embodiment, the wearable device 105B includes two discrete sensor areas, including one or more pressure sensors 110B on the base or bottom of the shoe (thereby arranged to collect data from the bottom of the user's foot), as well as one or more ankle sensors 115B located on or near the ankle portion of the wearable device 105B (thereby arranged to collect data from on the ankle of the user). In some embodiments, the wearable device 105B may include only the pressure sensors 110B, only the ankle sensors 115B, or both.

In some embodiments, as discussed above and below in more detail, the pressure sensors 110B can generally include one or more components that are configured to detect pressure (and indicate the amount of pressure), such as a pressure transducer that converts input mechanical pressure into an electrical output signal indicating the amount of pressure. In embodiments, the pressure sensor 110B can include a wide variety of sensor types, including strain gauge-based instruments (e.g., where a flexible element such as a thin metal strip or a film can be moved by the mechanical pressure, allowing for measurement of the pressure), capacitive sensors (e.g., where a diaphragm and/or pressure cavity is used to define a variable capacitor, where mechanical pressure can change the size of the cavity and thereby change the measured capacitance), a piezo-resistive sensor, and the like.

In at least one embodiment, the pressure sensor(s) 110B are integrated into the wearable device 105B, such that they are unobtrusive or imperceptible to the user. For example, the pressure sensors 110B may be thin components (e.g., thinner than a defined maximum depth, which may be determined based on user preference or experimentation) sewn into or otherwise included in the wearable device 105B (e.g., in the insole).

In some embodiments, the pressure sensors 110B may be powered and/or controlled locally. That is, the power source (if needed), communication systems (e.g., to transmit the pressure data to one or more other components), and the like may be included in the pressure sensors 110B themselves. In other embodiments, as discussed below in more detail, such components may be included on or with the ankle sensors 115B. In one such embodiment, one or more wires, cables, or other communication links may be provided to connect the pressure sensors 110B to the relevant other components (e.g., to a power source and wireless transmitter).

In the illustrated embodiment, the ankle sensors 115B are arranged on the ankle portion of the wearable device 105B, such that they will be proximate to the ankle of the user when the wearable device 105B is worn. In some embodiments, the ankle sensors 115B are included on the inner side of the user's ankle (e.g., on the medial side of the ankle or foot). In embodiments, the ankle sensors 115B can generally include a wide variety of sensors, such as gyroscopes, accelerometers, inertial sensors, blood pressure sensors, heart rate or pulse sensors, blood oxygen sensors, and the like.

In some embodiments, the ankle sensors 115B are integrated into the wearable device 105B in a similar manner to the pressure sensors 110B (e.g., sewn into the fabric of the shoe). In some embodiments, some or all of the ankle sensors 115B are included within one or more removable components. For example, the ankle sensors 115B may be enclosed within a sensor housing that is removably attached to the wearable device 105B, such as by inserting it into a sewn pocket, attaching it with a stretchable band, and the like. In some embodiments, the removable component can generally include any elements that are not washable or are otherwise sensitive. For example, if a given sensor (such as an accelerometer) can be safely washed (either by hand or in a washing machine), the given sensor may be integrated into the wearable device 105B. Other sensors or components which are not washable (e.g., blood pressure sensors, power sources, and the like) may be included in a removable component.

In some embodiments, as discussed above, the area of the ankle sensors 115B can also include any other needed components, such as a transmitter, a power source (e.g., a rechargeable or replaceable battery), and the like. In at least one embodiment, the ankle sensors 115B (or the unit or component including them) is a slim-line component (e.g., less than a defined maximum thickness) that renders it unobtrusive for the user (e.g., such that it does not interfere with ordinary walking).

In some embodiments, as discussed above, the ankle sensors 115B (or accompanying components such as power source and transmitter) may be communicatively coupled with the pressure sensors 110B. This communication link may include wireless connectivity (e.g., via a short-range radio communication), wired connectivity (e.g., via one or more wires or cables connecting the pressure sensors 110B to the ankle sensors 115B and/or other components), and the like.

Example Wearable Sensor Placement for Improved Fall Detection and Prevention

Figure 2:
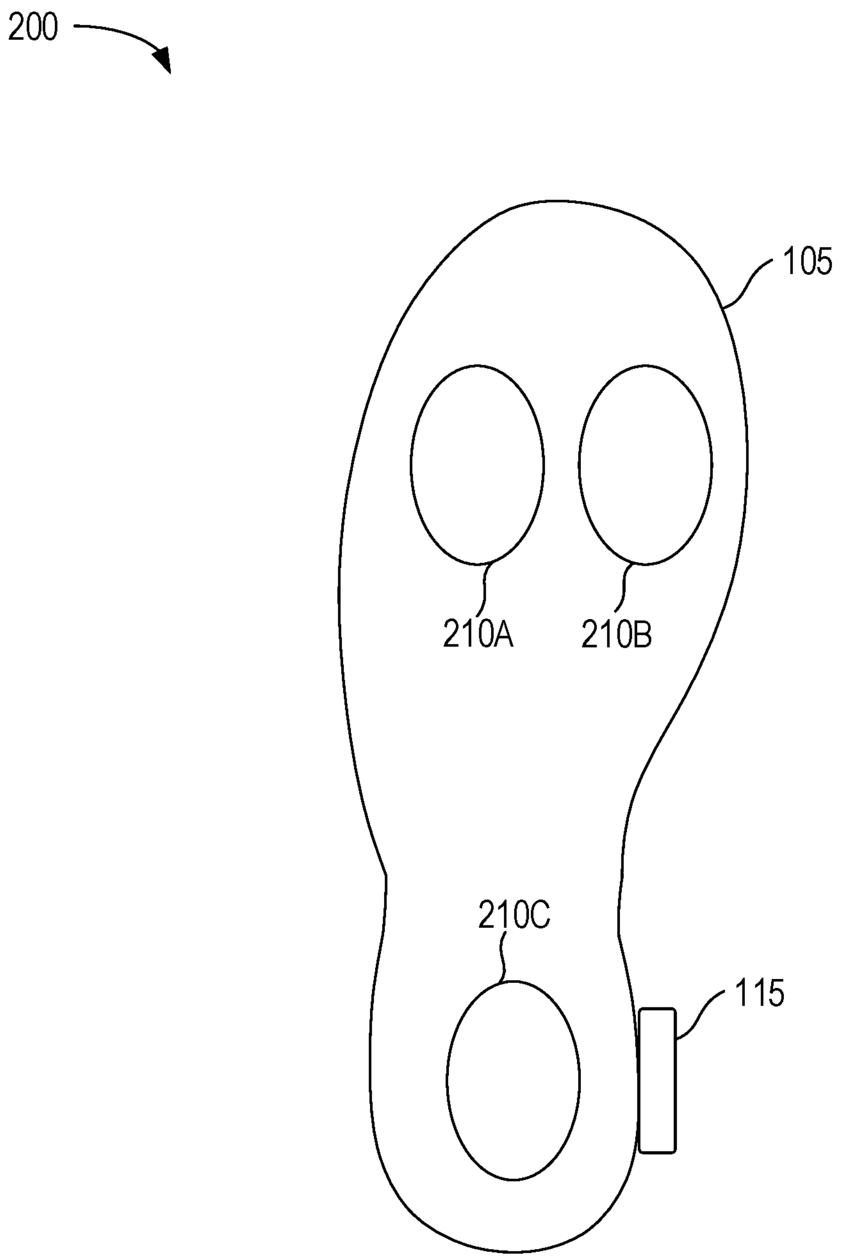
FIG. 2 depicts example wearable sensor placement for improved fall detection and prediction.

FIG. 2 depicts example wearable sensor 200 placement for improved fall detection and prediction.

Specifically, the illustrated example depicts a wearable device 105 (e.g., a smart sock, such as discussed above with reference to FIG. 1A, or a smart shoe, such as discussed above with reference to FIG. 1B) from the bottom of the device. In the illustrated example, the wearable device 105 includes three pressure sensors 210. Specifically, a first pressure sensor 210A is arranged to detect pressure for the outer (e.g., lateral) side of the ball of the user's foot (e.g., the lateral side of the padded portion of the sole between the toes and the arch, underneath the heads of the metatarsal bones). Further, the pressure sensor 210B is arranged to detect pressure for the medial side of the ball of the foot.

Advantageously, the pressure sensors 210A and 210B allow the wearable device 105 to transmit data indicating whether the user is distributing their weight equally or appropriately, or if they are leaning or rolling their foot towards the left or right.

In the illustrated example, the wearable device 105 also includes a pressure sensor 210C under the heel of the foot (e.g., under the padded cushion of fatty tissue around the heel bone). This pressure sensor 210C can be used to determine the amount of pressure the user is exerting under the heel (as compared to under the ball of the foot), and/or pressure differential between feet (e.g., with more or less pressure under the left foot than the right). Further, the pressure sensor 210C can be used to evaluate the user's walking cycle, such as whether they land their heel first followed by their toes, whether the ball of the foot lands first, whether the heel and ball land simultaneously (or within a defined time window), and the like.

As illustrated, the ankle sensor(s) 115 are arranged on the medial side of the ankle of the user. This can allow them to be unobtrusive (e.g., less likely to catch or snag on objects the user walks past), while simultaneously allowing them to record accurate data regarding the motion, orientation, and/or acceleration of the foot. Further, by arranging the sensors 115 on the inner side of the ankle, components such as blood pressure sensors can be arranged to capture data via the saphenous vein, which passes over the medial malleolus and runs up the medial side of the leg.

Although not depicted in the illustrated example, in some embodiments, as discussed above, the pressure sensors 210 may be communicatively linked to the ankle sensors 115 via one or more cables or wires to facilitate collection and transmission of the sensor data.

Example Ankle Unit for Improved Fall Detection and Prevention

Figure 3:
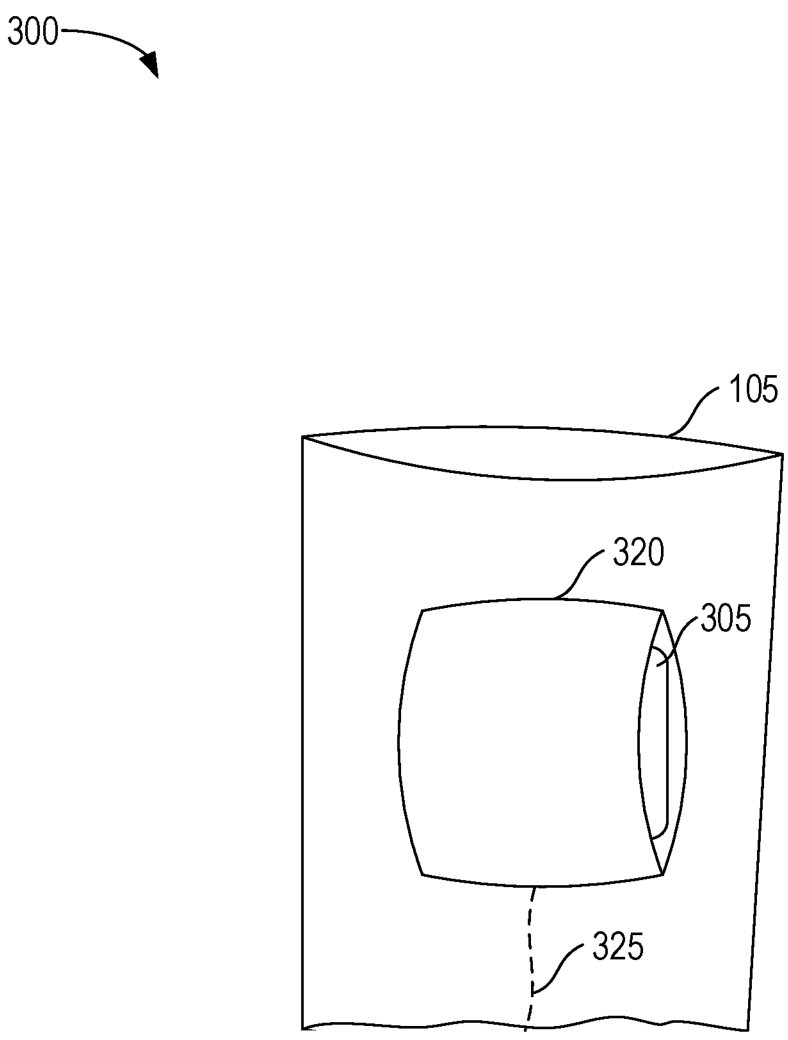
FIG. 3 depicts an example ankle unit for improved fall detection and prediction.

FIG. 3 depicts an example ankle unit 305 for improved fall detection and prediction.

The illustrated example depicts an upper or ankle portion of a wearable device 105, such as (e.g., a smart sock, such as discussed above with reference to FIG. 1A, or a smart shoe, such as discussed above with reference to FIG. 1B). In the illustrated example, the ankle portion of the wearable device 105 includes a pocket 320.

For example, if the wearable device 105 is a smart sock, the pocket 320 may be a stretchable fabric sewn onto the sock, such that objects (e.g., ankle units 305) can be inserted into the pocket and held in place (either by the fabric itself, or by one or more enclosure mechanisms such as a hook and loop connection). Although depicted as a pocket 320 for conceptual clarity, in embodiments, the ankle unit 305 can be connected to the wearable device 105 using any suitable connection technique, such as using an elastic or other stretchable band around the ankle, tied in place, held in place using hook and loop fasteners or other connective devices, and the like.

The ankle unit 305 can generally correspond to a component or unit that houses one or more ankle sensors (and, in some aspects, corresponding hardware such as a power source). One example of an ankle unit 305 is discussed in more detail below with reference to FIG. 4. In the illustrated embodiment, the ankle unit 305 is removable, detachable, separable, or otherwise not fixed to the wearable device 105. That is, a user can non-destructively separate the ankle unit 305 and wearable device 105, such that they can be similarly rejoined or reconnected. In some embodiments, the ankle unit 305 is removable without the need for any tools (e.g., a screwdriver).

For example, the ankle unit 305 may be slid into and out of the pocket 320 manually by the user (or by an assisting caregiver), may be connected via hook and loop fasteners by pressing the unit in place, may be slid or placed under or inside a stretchable band, and the like.

In the illustrated example, the ankle unit 305 can be coupled with a communication link 325, allowing it to interface with one or more pressure sensors on the bottom of the wearable device 105, as discussed above. For example, the communication link 325 may be a wire or cable integrated into the material of the wearable device 105 and terminating in or near the pocket 320. This can allow the ankle unit 305, which may include a power supply and/or wireless transmitter, to drive and enable use of the pressure sensors.

For example, the communication link 325 may be plugged into a physical port on the ankle unit 305, may be connected via a magnetic port (e.g., held in place by magnets to enable data and/or power transmission), and the like. In some embodiments, the communication link 325 can be plugged manually into the ankle unit 305 when the unit is inserted to the pocket 320 or otherwise attached to the wearable device 105. In at least one embodiment, the communication link 325 can be automatically and effortlessly connected when the ankle unit 305 is inserted, such as via one or more magnets in the communication link 325 that are magnetically attracted to one or more magnets in the ankle unit 305. This may also allow the ankle unit 305 to be easily removed from the wearable device 105 (e.g., to wash the wearable device 105, to charge the ankle unit 305, and the like).

Example Sensor Unit for Improved Fall Detection and Prevention

Figure 4:
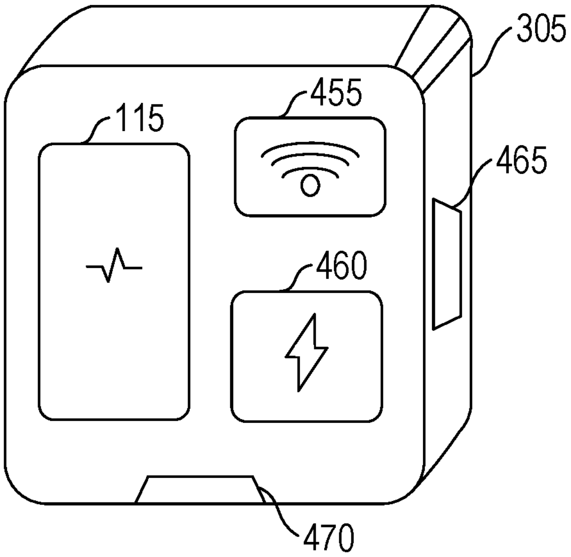
FIG. 4 depicts an example sensor unit for improved fall detection and prediction.

FIG. 4 depicts an example ankle unit 305 for improved fall detection and prediction. The illustrated example provides additional detail for one or more aspects of the ankle unit discussed above with reference to FIG. 3.

In the illustrated example, the ankle unit 305 is an integrated or discrete component (e.g., enclosed in a plastic or metal housing) to contain a set of components for a wearable device (such as the smart sock discussed above with reference to FIG. 1A and/or the smart shoe discussed above with reference to FIG. 1B). In some embodiments, the ankle unit 305 is removable as discussed above. This can allow easy charging of the ankle unit 305, facilitate swapping the ankle unit 305 between wearable devices, and the like. For example, in one such embodiment, a user may possess or be assigned two ankle units 305 (one for each foot), and the user may freely insert or attach the ankle units 305 to the specific socks, shoes, or other wearable devices that they desire at any given day or time. This can allow the user to use a multitude of different wearables while maintaining a relatively smaller set of ankle units 305, thereby reducing the cost associated with the devices (as well as reducing the time required to maintain each, such as by daily charging).

In the illustrated example, the ankle unit 305 includes one or more ankle sensors 115 (e.g., accelerometers, gyroscopes, blood pressure sensors, and the like). As illustrated, the ankle unit 305 further includes one or more power sources 460 (e.g., batteries). The power source 460 can generally correspond to any suitable source of electrical power, such as one or more rechargeable batteries (e.g., made using nickel-cadmium (NiCd), nickel-metal hydride (NiMH), lithium-ion (Li-ion), lithium-polymer (Lipo), and the like). In some embodiments, the power source 460 can include non-rechargeable batteries (e.g., single use batteries which can be removed and replaced with new batteries). In at least one embodiment, the power source 460 can additionally or alternatively include components to recharge batteries and/or directly provide power, such as one or more solar cells, piezoelectric generators, and the like.

In the illustrated example, the ankle unit 305 further includes one or more transmitters and/or receivers 455 (also referred to as transceivers in some aspects). The transmitter 455 can generally correspond to any component or technique for transmitting the collected sensor data, such as wireless communications (e.g., using short-range radio such as Bluetooth®, or more long-range radio such as Wi-Fi™ or a cellular connection). In some embodiments, the transmitter 455 corresponds to a wired connection, such as via one or more wires or cables from the ankle unit 305 to a user device, such as a smartphone.

In some embodiments, the transmitter 455 transmits the sensor data (e.g., from the ankle sensors 115 and pressure sensors) continuously as it is recorded/received. In some embodiments, the transmitter 455 transmits the sensor data periodically (e.g., transmitting blocks of data every five minutes). In some embodiments, the transmitter 455 transmits the data upon request or other event (e.g., when the user indicates to transmit the data using a button or other input, when the user plugs the ankle unit 305 into a computing device such as a laptop, when a remote server requests updated sensor data, and the like).

In the illustrated example, the ankle unit 305 can also include one or more ports 465 and 470. In at least one example, the port 465 may be used to charge the power source 460, to receive sensor data or other data relating to the ankle unit 305 (e.g., unique identifiers), and/or to provide data to the ankle unit 305 (e.g., to reprogram it). For example, in one such embodiment, the port 465 may correspond to a universal serial bus (USB) port, such as a USB-A port, a USB-B port, a USB-B mini port, a USB-B micro port, a USB-C port, and the like.

In some embodiments, users may use the port 465 to connect the ankle unit 305 to a power source (e.g., to charge the unit), to download data off the device, and/or to upload data (e.g., new firmware) to the device.

In the illustrated example, the port 470 may be optionally used to connect the ankle unit 305 to one or more pressure sensors, as discussed above. For example, a communication link from the pressure sensor(s) may be magnetically coupled with the port 470, allowing for easy and hands-off installation of the ankle unit 305. Although depicted as discrete ports 465 and 470 for conceptual clarity, in at least one embodiment, the port 465 and 470 may be combined into a single port.

As discussed above, the ankle unit 305 can generally be removably attached to one or more wearable devices, allowing the ankle unit 305 to collect and transmit sensor data, such as accelerometer data, gyroscope data, and/or blood pressure data from the user's ankle, as well as pressure data from the user's foot. This sensor data may be transmitted to a variety of systems, as discussed in more detail below, to enable a wide variety of analyses and actions to be taken.

Example Environment for Machine Learning to Evaluate Sensor Data

Figure 5:
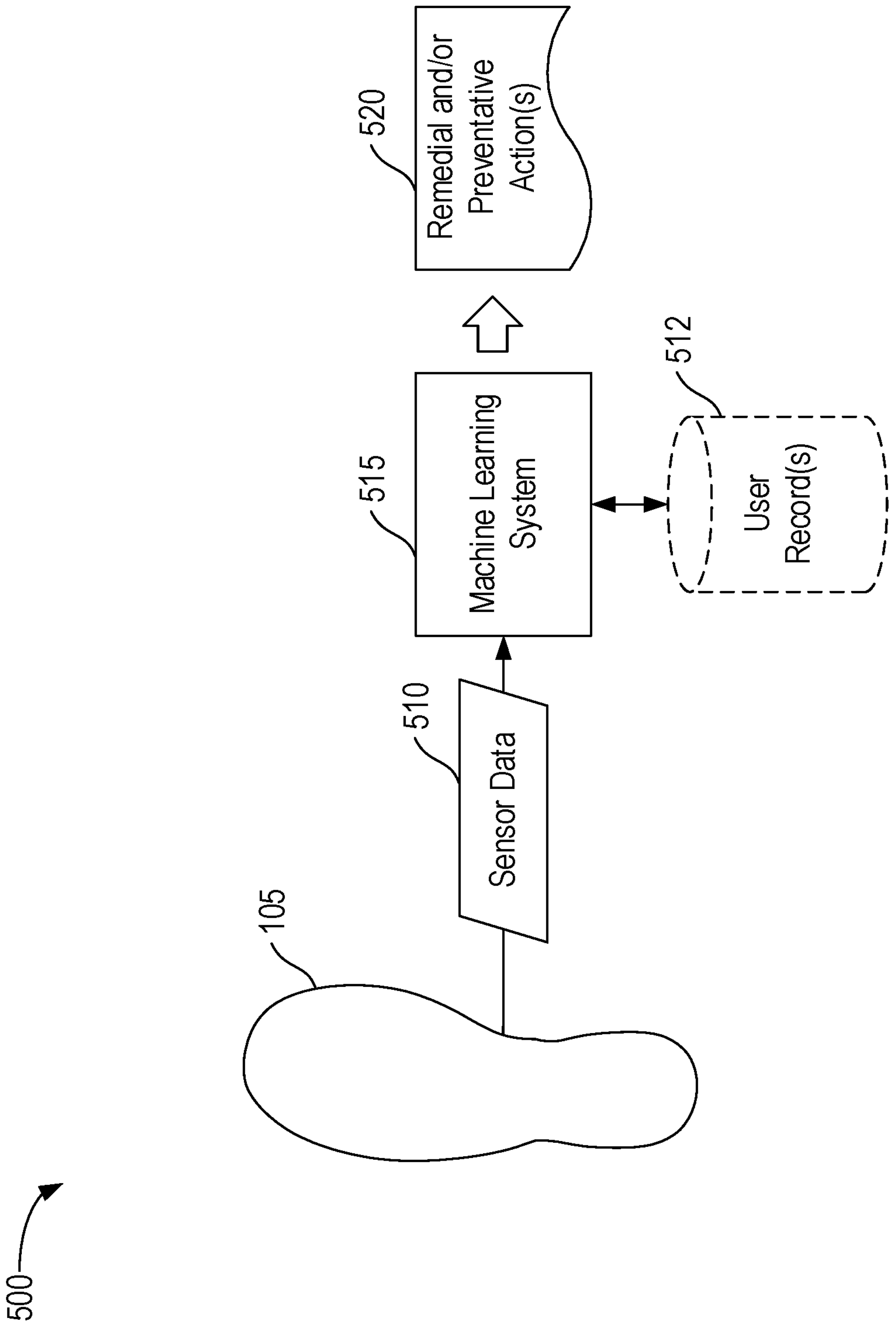
FIG. 5 depicts an example environment for using machine learning to evaluate sensor data and predict fall events.

FIG. 5 depicts an example environment 500 for using machine learning to evaluate sensor data and predict fall events.

In the illustrated environment 500, a set of one or more wearable devices 105 are configured to record sensor data (e.g., pressure data, motion data, blood pressure data, and the like) from one or more feet and/or ankles of a user. In some embodiments, the wearable devices 105 correspond to foot-worn items, as discussed above. For example, the sensors may be included in smart socks and/or shoes, in insoles that are inserted into the user's shoes, and the like. In embodiments, there may be any number of wearable devices 105 used in the environment 500. For example, the system may use two wearable devices 105: one for each of the user's feet.

As illustrated, the wearable devices 105 transmit or otherwise provide sensor data 510 to a machine learning system 515. In various embodiments, this sensor data 510 may be provided using any suitable technology, including wired or wireless communications. For example, in one embodiment, the wearable devices 105 can use cellular communication technology to transmit the sensor data 510 to the machine learning system 515. In some embodiments, the wearable devices 105 use one or more local wireless networks (such as a WiFi network, a Near Field Communication (NFC) network, a Bluetooth network, etc.) to transmit the sensor data 510. In at least one embodiment, the wearable devices 105 can transmit the sensor data 510 to one or more intermediary devices, which can then forward the data to the machine learning system 515. For example, the wearable devices 105 may transmit the sensor data 510 to a smartphone, tablet, or other device associated with the user (e.g., via Bluetooth), and this user device can forward the data to the machine learning system 515 (e.g., via WiFi or a cellular connection).

In some embodiments, the sensor data 510 is transmitted over one or more networks including the Internet. That is, the machine learning system 515 may reside at a location remote from the user and wearable devices 105 (e.g., in the cloud). Though a single wearable device 105 is illustrated for conceptual clarity, in embodiments, data from any number and variety of wearable devices 105 (and any number of users) can similarly be provided to the machine learning system 515.

In embodiments, the machine learning system 515 can generally train one or more machine learning models to analyze the sensor data 510, and/or use trained models to evaluate the sensor data 510. In the illustrated example, the machine learning system 515 can also optionally receive a set of user records 512. For example, in some embodiments, the user records 512 can include information relating to various characteristics of the users associated with the wearable devices 105 (e.g., the residents in a residential facility). For example, the user records 512 may indicate, for each user, which wearable device(s) 105 are associated with the given user, as well as characteristics such as their age, height, weight, whether they use an assistive device such as a cane or walker, whether they have suffered a fall (and if so, details relating to the fall, such as the time, severity, direction, cause, etc.), and the like.

In some embodiments, the user record(s) 512 are used as input, alongside the sensor data 510, when training the model(s), as well as when using them to predict fall events. That is, the sensor data 510 from a user, along with one or more of the characteristics indicated in the corresponding user record(s) 512 for the user, may be used as input to the model(s) to generate predicted fall characteristics (e.g., timing, severity, and the like). During inferencing, this output can be used to drive a variety of interventions, as discussed in more detail below. During training, this output can be compared against a known label (e.g., indicating whether the user fell) in order to compute a loss used to refine the model(s).

As used herein, the loss generally corresponds to the difference between the actual model output and the target output. In embodiments, the loss may be computed using a variety of algorithms or techniques, including cross-entropy loss, mean absolute error, and the like. Generally, the magnitude of the difference is directly correlated with the magnitude of the loss. The loss is used to refine the internal parameters of the model(s), such as the weights and/or biases. Generally, the magnitude of the loss is directly correlated with the magnitude of the change needed for these parameters. Thus, by iteratively generating losses (using one or more sets of training data), the system can iteratively refine the parameters to generate more accurate predictions.

In at least one embodiment, the machine learning system 515 can use machine learning to predict a variety of fall-related events, such as a likelihood of a future fall (which may include an imminent fall, such as due to stumbling, as well as falls further into the future, such as due to degrading balance over time), a potential severity of the future fall, and the like. In some embodiments, a separate machine learning model is trained for each such output. This may allow the model(s) to specialize for their particular target output. For example, predicting whether a fall will occur may involve different features (or differently-weighted features), as compared to predicting when the fall will occur and/or how severe the fall will be. By training a separate model for each such output, the system allows each model to learn the particularized parameters that are best-suited to accurately predict the particular output.

In one embodiment, to train the models, the machine learning system 515 can collect sensor data 510 and/or user record(s) 512 over time from any number of users. For example, each user in a facility (e.g., a long term care unit) can have an associated set of wearable devices 105 (e.g., a pair of sensor-equipped smart socks or shoes), and the sensor data from each user can be used to train the models. In at least one embodiment, the machine learning system 515 or another component can monitor the environment to tag this sensor data based on a variety of factors, including the characteristics of the corresponding user (e.g., age, weight, height, and the like).

In some embodiments, the data is associated with a "ground-truth" label based on whether the corresponding user suffered a fall. For example, each time a participating user falls (e.g., as indicated in the user records 512), the machine learning system 515 (or another system) can retrieve the corresponding records of sensor data 510 from that user for one or more prior times (e.g., for N seconds, minutes, hours, or days prior to the fall), and label this data as indicative that a fall is imminent. In at least one embodiment, the label further indicates how much time elapsed between the sensor reading and the fall. For example, a first record may be labeled to indicate that the user fell five minutes after the data was recorded, while a second record indicates that the user fell thirty seconds later.

In at least one embodiment, the sensor data 510 may additionally or alternatively be labeled to indicate various aspects of the fall, such as the direction of the fall (e.g., to the left, to the right, forward, backwards, and the like). Similarly, the data may be labeled to indicate the severity of the fall (e.g., whether it resulted in any broken bones or other injuries, the extent of these injuries, and the like). In at least one embodiment, the data can additionally or alternative be tagged using contextual data that may be relevant in predicting similar falls. For example, using video or images of the fall (captured by one or more cameras), the system may discern whether the patient tripped on an object, whether the user was actually using any assistive device such as a cane, and the like. This information can allow the system to generate more robust training data that more accurately accounts for the particular context of the fall.

By collecting such data over time and from a variety of users, the machine learning system 515 is able to automatically build a training data set that can be used to train or refine a variety of machine learning architectures to predict future falls, how far into the future the fall will occur, which direction the user will fall, how severe the fall may be, and the like.

In at least one embodiment, if a given user does not fall (or does not fall within some defined window), the machine learning system 515 can automatically label the corresponding records as not indicative of an upcoming fall. For example, the machine learning system 515 may continuously or periodically identify unlabeled sensor records (e.g., records that have not already been labeled as preceding a fall) that are older than a user-defined threshold (e.g., older than a week), and label these records as not indicative of a fall (if no fall is reported in the user records 512). In this way, the machine learning system 515 can generate both positive training samples (e.g., sensor data 510 and/or user characteristics that indicate that a fall is imminent) as well as negative training data (e.g., sensor data 510 and/or user characteristics that indicate that the user is steady and/or a fall is not imminent).

In some embodiments, as discussed above, the machine learning system 515 can train a number of machine learning models to address a variety of desired predictions. For example, a first model may be trained to predict if a user will fall, while a second is used to predict how far into the future the fall will occur. In some aspects, a first model may be trained to predict imminent falls (e.g., within the next M seconds, based on a narrow window of input time), while others are trained using progressively longer intervals for more distant predictions (e.g., evaluating data collected over an hour to determine whether a fall is likely in the next hour). Other models may be used to predict fall direction, fall severity, and the like.

Generally, training the machine learning models includes providing some set of sensor data 510 from one or more users as input to the model (e.g., sensor data covering a defined window of time) to generate some predicted output. In some embodiments, the input also includes one or more characteristics of the user (such as age, whether they use an assistive device, and the like), as discussed above. At early stages of training, this output may be relatively random or unreliable (e.g., due to the random weights and/or biases used to initiate the model). The generated output can then be compared against the relevant label for which the model is being trained (e.g., whether a fall occurred, how severe the fall was, and the like) to generate a loss, and the loss can be used to refine the model (e.g., using back propagation in the case of a neural network). Generally, this refinement process may be performed individually for each user or window of time (e.g., using stochastic gradient descent) or in batches (e.g., using batch gradient descent). Further, in embodiments, the machine learning system 515 can train models to operate on windows of data (e.g., a collection of discrete or continuous sensor values) or based on single records (e.g., sensor data at a given moment in time).

In an embodiment, once the model(s) are trained, the machine learning system 515 can deploy them for use in real-time. In one embodiment, as discussed above, the models may be trained on one or more systems and deployed to one or more other systems. In other embodiments, the machine learning system 515 can both train the models and use them for inferencing.

In some embodiments, during inferencing, the machine learning system 515 receives sensor data 510 in real-time (or near real-time) from participating users. In at least one embodiment, the machine learning system 515 also receives user record(s) 512 for the specific user. As used herein, inferencing refers to the stage of model deployment where the model(s) have been trained and are deployed for use in evaluating actual input during runtime. As the model output may be referred to in some embodiments as "inferences," this stage may be referred to as "inferencing." During inferencing, the machine learning system 515 can process this sensor data (along with, in some embodiments, user characteristics such as age) using one or more of the trained models in order to predict potential falls.

In at least one embodiment, the machine learning system 515 can process the data sequentially using the models, rather than using all models in parallel. This may significantly reduce computational expense of evaluating the sensor data 510, thereby reducing the needed memory space and computational power, as well as reducing energy consumption and latency (e.g., if the system becomes overloaded from a large number of users).

For example, the machine learning system 515 may first use an initial model (e.g., to determine whether a fall is imminent). If a fall is determined to be imminent, the machine learning system 515 may immediately initiate remedial or preventative actions, as discussed in more detail below. The fall severity, direction, and other characteristics of the potential fall may be predicted later, or may be bypassed entirely (e.g., as irrelevant once the fall occurs or does not occur). In one such embodiment, if a fall is not imminent but may occur at some point in the future, the machine learning system 515 can selectively use one or more other models to predict the nature of the fall, such as when it will occur, the direction the user will fall, the severity, and the like.

If no fall is predicted, the machine learning system 515 can refrain from initiating any further action. However, in the illustrated example, if a fall is predicted, the machine learning system 515 can initiate a wide variety of remedial and/or preventative actions. For example, if a fall is imminent (e.g., within a defined number of seconds or minutes), the machine learning system 515 may initiate actions such as instructing the user to sit or grasp an object for support, alerting nearby caregivers to attend to the user immediately, and the like.

In some embodiments, if the predicted fall is more remote (e.g., more than a defined number of minutes in the future), the machine learning system 515 can initiate other remedial actions, such as suggesting or prescribing medical devices including canes, walkers, and wheelchairs. In some embodiments, the machine learning system 515 can suggest or prescribe one or more physical therapy plans or changes based on the prediction. For example, if the machine learning system 515 predicts that the user may fall towards their left, the machine learning system 515 may determine that physical therapy is needed to strengthen the user's muscles on the left side of their body (or to otherwise correct any pains or other concerns on this side). In response, the machine learning system 515 can suggest or initiate physical therapy to correct these concerns.

In at least one embodiment, based on aggregated fall predictions or detections, the machine learning system 515 can additionally or alternatively provide facility-wide remedial or preventative actions 520. For example, if a number of falls (or predicted falls) occur in a given area (e.g., if the machine learning system 515 observes that users stumble in a given place in the facility, such that predicted imminent falls increase on average in this place), the machine learning system 515 may flag this area for manual review. This may indicate, for example, that there is a hazard in the area (e.g., a rug pulling up or a cable across the floor).

In embodiments, by providing these targeted and user-specific interventions (including immediate assistance as well as more preventative and long-term care such as medical devices and physical therapy), the machine learning system 515 is able to dramatically reduce falls (and fall severity), thereby improving user results. Further, by iteratively using some machine learning models only when the output from a prior model satisfies certain criteria, the machine learning system 515 can provide this granular and specific analysis using reduced computational resources and expense.

Figure 6:
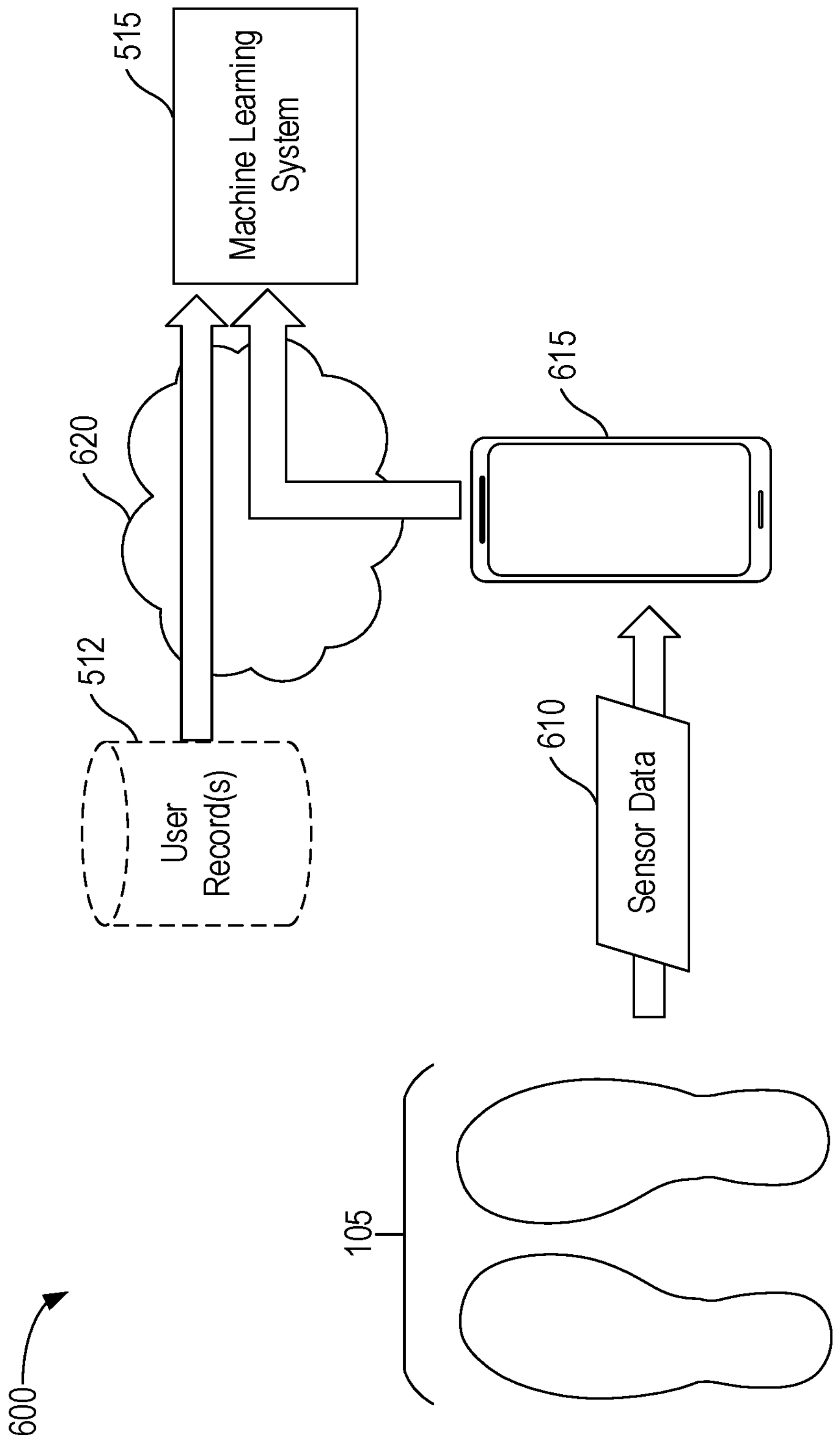
FIG. 6 depicts an example environment for using an intermediate communication device and machine learning to evaluate sensor data and predict fall events.

Example Environment for Using an Intermediate Communication Device and Machine Learning to Evaluate Sensor Data and Predict Fall Events FIG. 6 depicts an example environment 600 for using an intermediate communication device and machine learning to evaluate sensor data and predict fall events.

In the illustrated environment 600, a set of wearable devices 105 (e.g., one or more devices on each foot, where each device can include one or more physical sensors) are configured to record sensor data from the feet of a user. For example, as discussed above, the wearable devices 105 may include smart socks, smart shoes, components that can be included or attached to insoles, socks, or shoes, and the like.

In the illustrated environment 600, the wearable devices 105 are configured to transmit or otherwise provide sensor data 610 to a user device 615, which can then forward the sensor data 610 (and, in some embodiments, other relevant data) to the machine learning system 515. That is, while in the environment 500, the wearable devices 105 may transmit the sensor data directly to the machine learning system 515, the environment 600 uses a user device 615 of the user.

In the illustrated example, the user device 615 is a smartphone. However, in embodiments, other devices may be used. Generally, the user device 615 corresponds to a portable computing device associated with the user (such as a phone, tablet, smart watch, and the like). The user (or an assisting person, such as a caregiver) may use the user device 615 to link the wearable devices 105 to the corresponding user and user device 615. For example, the user may use short-range wireless technology such as Bluetooth to pair the user device 615 and the wearable devices 105 (e.g., via one or more ankle units, such as ankle unit 305 of FIGS. 3 and 4). The wearable devices 105 can then transmit sensor data 610 to the user device 615, which can optionally tag it based on user characteristics such as the identity of the user, the user's age, and the like.

In the illustrated example, the user device 615 then forwards the sensor data 610 to the machine learning system 515 via a network 620 (e.g., the Internet). In the illustrated example, the user records 512 are separately provided to the machine learning system 515 via the network 620. In at least one embodiment, the user records 512 are alternatively or additionally provided by the user device 615.

For example, the user device 615 may tag the sensor data 610 with a unique identifier of the user, and the machine learning system 515 may use this identifier to retrieve or determine the corresponding user record(s) 512 containing information relevant to the user. Alternatively, the user device 615 may directly include some or all of this information, such as the user's age, height, weight, and the like.

In embodiments, as discussed above, the machine learning system 515 can generally train one or more machine learning models to analyze the sensor data 610 and user records 512, and/or use trained models to evaluate the sensor data 510 and user records 512. For example, as discussed above, the sensor data 610 and user records 512 may be used as input to generate a predicted output (e.g., a fall likelihood or a fall severity), which can be evaluated against the ground truth label (e.g., determined from the user records 512) to refine the model(s). Once trained, as discussed above, the machine learning system 515 may process the sensor data 610 and user records 512 using the model(s) to predict whether a fall is likely for each given user, the potential severity of the fall, and the like.

Figure 7:
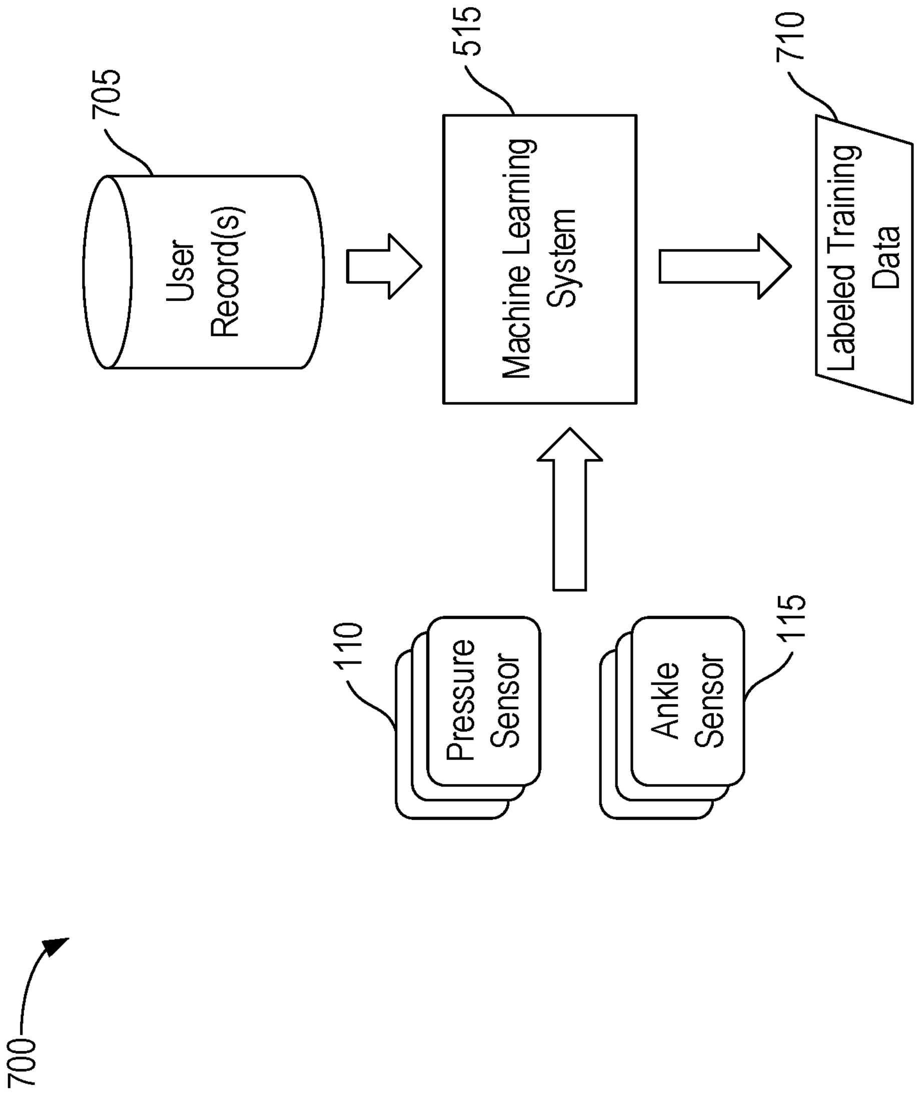
FIG. 7 depicts an example workflow for generating labeled data to train machine learning models to predict fall events.

Example Workflow for Generating Labeled Data to Train Machine Learning Models to Predict Fall Events FIG. 7 depicts an example workflow 700 for generating labeled data to train machine learning models to predict fall events.

In the illustrated workflow 700, the machine learning system 515 receives data from one or more pressure sensors 110 and one or more ankle sensors 115, as discussed above. For example, the pressure sensors 110 and ankle sensors 115 may be included as part of one or more wearable devices, such as smart socks, smart shoes, ankle units, and the like. For example, one or more wearable devices may transmit the pressure data and/or ankle data continuously, periodically (e.g., every second, every five seconds, etc.), and the like. In one embodiment, as the sensor data is received, the machine learning system 515 can tag it or otherwise associate it with the corresponding user. For example, the machine learning system 515 can identify the corresponding user record(s) 705 (e.g., based on an identifier included in the sensor data), such that the sensor data can be associated with relevant user characteristics that are used as input to the models, such as age, weight, and the like. In some embodiments, as discussed above, the received sensor data already includes such characteristics. In the illustrated workflow 700, the machine learning system 515 may store this (tagged) sensor data for future labeling, as discussed below in more detail.

In some embodiments, the machine learning system 515 can evaluate the user records 705 periodically, continuously, or upon specified events in order to label the sensor data. For example, the machine learning system 515 may periodically evaluate the user record(s) 705 for the registered users (e.g., daily or weekly) in order to determine whether any of the user(s) suffered a fall. In some embodiments, the machine learning system 515 can receive fall information automatically (e.g., as a pushed alert or notification, rather than by actively checking the records for fall reports). In some embodiments, the falls may be reported manually (e.g., by the user or by a caregiver). In at least one embodiment, the system can automatically detect falls, as discussed above (e.g., based on changes in the pressure data, motion data, orientation data, and the like for one or more of the user's feet).

If a fall is indicated in the user records 705, the machine learning system 515 can retrieve one or more corresponding records of sensor data, and label it to indicate the fall. For example, as discussed above, the machine learning system 515 can label each sensor record to indicate information such as the fact that a fall occurred, how far into the future (relative to the record) the fall occurred, the direction of the fall, the severity of the fall, and the like. In some embodiments, the machine learning system 515 can label a sequence of sensor records in this way. For example, one record may be labeled to indicate that it immediately preceded a fall (e.g., within a defined period of time), while a second is labeled to indicate that a fall occurred one hour after the sensor data was recorded. This can allow the machine learning system 515 to train a set of model(s) to predict when the fall will occur.

In the illustrated workflow 700, the machine learning system 515 can then store the sensor data as labeled training data 710. As discussed above, this labeled training data 710 can be used to train and/or refine one or more machine learning models. In various embodiments, this training may be performed periodically (e.g., weekly), or upon specified events. For example, in at least one embodiment, if a fall occurs, the machine learning system 515 can determine whether the model(s) predicted the fall (or would have predicted it, if they were not used to evaluate the sensor data). If the model(s) accurately predicted the fall and/or fall characteristics, the machine learning system 515 can label and store the data for subsequent refinement. In some embodiments, if the model(s) failed to predict the fall and/or characteristics, the machine learning system 515 may immediately use the data (and any other labeled training data 710 that has not-yet been used to train the model(s)) to refine the model(s) for more accurate predictions.

In some embodiments, in addition to positive labeled training data 710 (e.g., samples that preceded a fall), the machine learning system 515 can also generate labeled training data 710 corresponding to negative examples. For example, the machine learning system 515 may periodically or continuously identify sensor data that is older than some defined threshold (e.g., more than a week old). If the user records 705 do not indicate that the user fell in that defined window, the machine learning system 515 may automatically label the sensor data as not indicative of an upcoming fall. These negative samples can then be stored as labeled training data 710 for future training and/or refinement, as discussed above.

As discussed above, these negative exemplars may also be used periodically (e.g., weekly), or upon specified events. For example, in at least one embodiment, if the model(s) predict a fall (or predict specific fall characteristics) but one does not occur (or the fall characteristics differ), the machine learning system 515 may immediately use the data (and any other labeled training data 710 that has not-yet been used to train the model(s)) to refine the model(s) for more accurate predictions.

In this way, the machine learning system 515 is able to automatically generate labeled training data 710 for training and refining of the machine learning model(s). This automated label generation is efficient and rapid, and further can generally result in labeled training data 710 with reduced error (e.g., mislabeled data). As machine learning models generally require vast amounts of training data, this automated workflow 700 can enable training more accurate models than would be possible using conventional systems (e.g., that rely on manually-curated data). These more accurate models, in turn, can be used for significantly improved fall prediction and intervention.

Example Floorplan with Determined Fall Risk Areas Indicated

Figure 8:
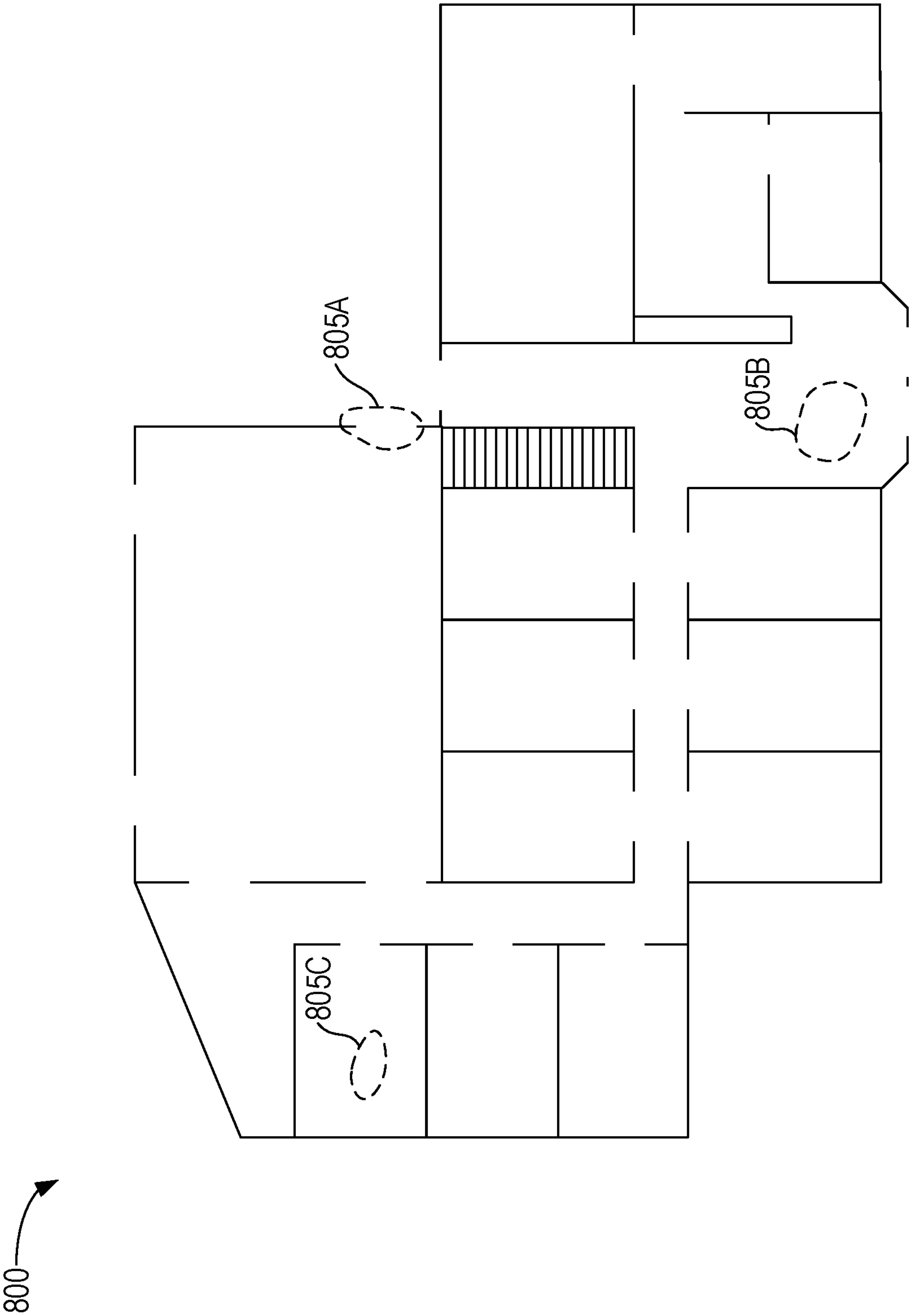
FIG. 8 depicts an example floorplan with determined fall risk areas indicated.

FIG. 8 depicts an example floorplan 800 with determined fall risk areas indicated. In some embodiments, the floorplan

800 may be generated and/or augmented by a machine learning system, such as the machine learning system 515 of FIG. 5.

In some embodiments, as discussed above, the machine learning system (or another system or device) can aggregate the fall predictions and/or events in order to provide deeper insights regarding potential fall hazards in one or more physical spaces or locations. In the illustrated example, the floorplan 800 corresponds to a residential facility (e.g., a nursing home or long term care facility) where users reside. However, in embodiments, the techniques described herein can be readily applied to a wide variety of locations and facilities.

In the illustrated example, three areas, locations, or regions are indicated by dashed-line circles 805A-C to indicate that they may be high risk areas. In some embodiments, to identify these areas, the machine learning system can evaluate reported fall(s) and/or predicted fall(s) for the facility. For example, for each reported (actual) fall, the machine learning system can determine where, in the facility, the fall occurred. This data may be used to generate augmented floorplans (e.g., using a heat map) indicating area(s) where falls occur more frequently.

In some embodiments, the machine learning system can additionally or alternatively aggregate predicted fall data to indicate problem areas. For example, each time the machine learning model(s) predict that a fall is imminent (e.g., due to a user stumbling), the machine learning system can determine where the predicted fall occurred (even if no actual fall follows). By similarly aggregating these predicted falls across the facility, the machine learning system can identify area(s) where falls are frequently predicted or close to occurring, even if no fall occurs. This data may similarly be output, such as via an augmented floorplan (e.g., using a heat map) to indicate these problem areas.

For example, in the illustrated floorplan 800, an area 805A is indicated as potentially problematic (e.g., due to the number or frequency of actual falls or predicted falls in that area). In embodiments, the particular technique used to indicate the areas 805 may vary depending on the particular implementation. For example, the machine learning system may generate a heat map, to be output via a graphical user interface (GUI). In some embodiments, the machine learning system can identify area(s) where the actual and/or predicted falls meet one or more defined criteria (e.g., a number of reported or predicted events, a frequency of the events, and the like), and indicate these areas specifically, such as by highlighting them, outlining them, and the like.

Based on the floorplan 800, it may be inferred that the area 805A is potentially hazardous due to, for example, a change in floor height between the inside and space and outdoor space, a height of the threshold in the doorway, and the like. Based on this information, a user or manager may investigate the area and/or take remedial actions if needed, such as by installing signage warning of a drop, lowering the height of the door threshold, adding hand rails, installing a ramp, and the like.

In the illustrated example, the area 805B is also indicated as potentially hazardous. For example, this area 805B may correspond to a place where the rug has lifted or come loose, where a cable or other obstacle crosses the room, and the like. As above, the user or manager can similarly investigate the area 805A to identify the hazard, and take appropriate remedial actions.

As illustrated, the machine learning system has also flagged the area 805C as potentially hazardous. Notably, this area 805C is within a room assigned to a specific user. That is, while the areas 805A and 805B are in public regions that may be generally accessible to the users, the area 805C may be in a private room where one or more residents generally reside (e.g., where they sleep and store their items). In some embodiments, as discussed above, the indication of this area may generally allow a user or manager to investigate the area 805C to identify potential hazards (such as furniture or other objects, cords, rugs, and the like).

In at least one embodiment, the machine learning system or user may infer that the particular user(s) associated with the area 805C may need assistance. That is, in addition to or rather than determining that the area itself is hazardous, the machine learning system may determine or infer that the corresponding user who lives in the room is frequently having difficulties with balance, such as when standing up from a chair or getting out of bed. In this way, the machine learning system can take preventative actions for the specific user(s), such as suggesting or instructing that a caregiver be present to assist in standing or sitting, or suggesting or assigning physical therapy tasks, as discussed above.

In this way, by aggregating the fall events and/or predicted fall events, the machine learning system can derive deeper insights regarding the facility and its users, and thereby significantly improve the safety of the facility and reduce potential harm.

Figure 9:
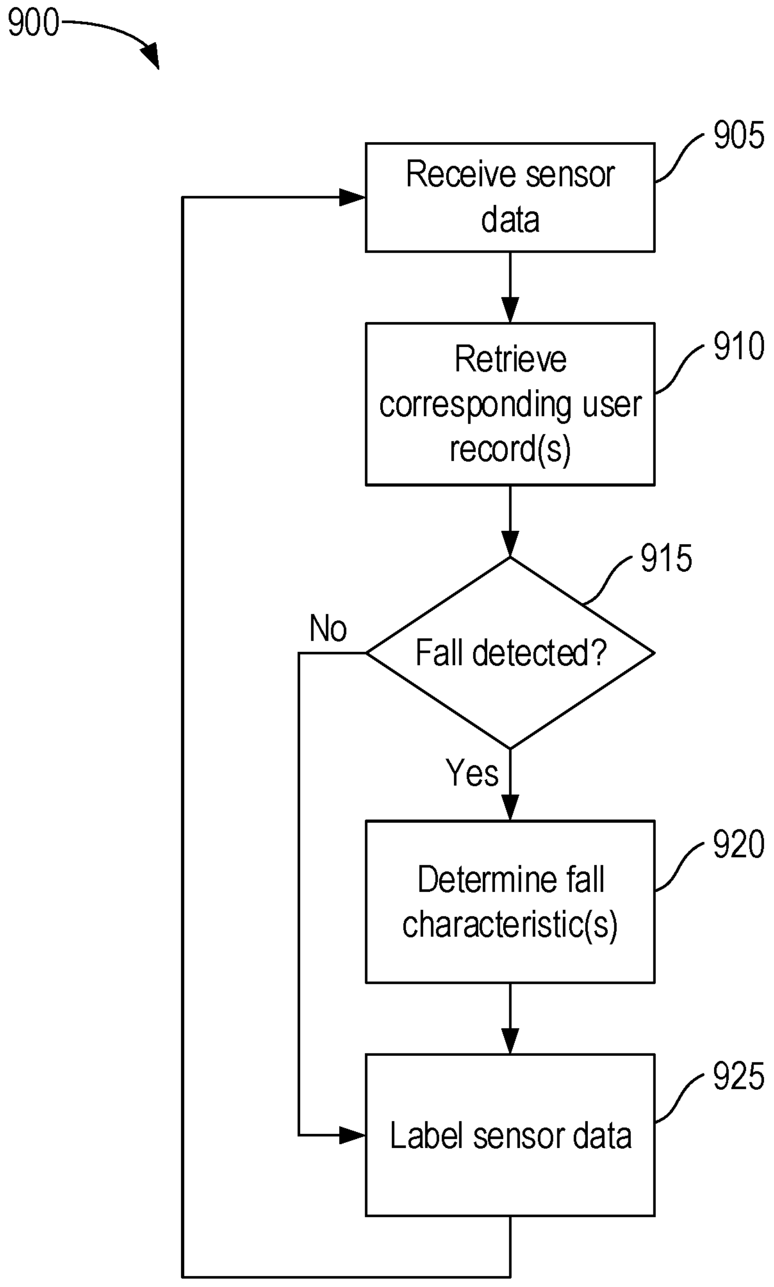
FIG. 9 is a flow diagram depicting an example method for generating labeled data to train machine learning models to predict falls.

Example Method for Generating Labeled Data to Train Machine Learning Models to Predict Falls FIG. 9 is a flow diagram depicting an example method 900 for generating labeled data to train machine learning models to predict falls. In some embodiments, the method 900 is performed by a machine learning system, such as machine learning system 515 of FIG. 5. In one embodiment, the method 900 provides additional detail for the workflow 700 of FIG. 7.

At block 905, the machine learning system receives sensor data from one or more sensors (e.g., from pressure sensors and/or ankle sensors included as part of one or more wearable devices, such as the wearable device 105 of FIGS. 1A, 1B, 2, and/or 3). For example, as discussed above, the machine learning system may be configured to receive sensor data continuously or periodically from one or more sensors associated with one or more users. In some embodiments, the sensor data can also include or be associated with various user data, such as a user identifier, characteristics of the user, and the like.

At block 910, the machine learning system retrieves one or more corresponding user record(s) for the user associated with the received sensor data. For example, based on a user ID included with the sensor data, the machine learning system can query one or more repositories to retrieve user records for the user, where these records can indicate various characteristics of the user (e.g., their age, height, weight, whether they use assistive devices, and the like). In some embodiments, the user records can additionally or alternatively indicate events, such as falls, that occurred. For example, each time a user falls (or, in some embodiments, almost falls), the user record(s) may be updated (e.g., by a caregiver, or automatically based on the sensor data) to indicate the event.

In some embodiments, the machine learning system performs block 910 when the sensor data is received. For example, if the sensor data is from one or more prior times (e.g., the data was not provided live, immediately after being recorded), the machine learning system may immediately retrieve the corresponding records. In some embodiments, if the sensor data was received live (e.g., shortly after being recorded), the machine learning system may store the data and subsequently retrieve the user records upon occurrence of one or more defined criteria (e.g., after a defined period of time has passed, upon being informed that a fall occurred and the like).

At block 915, the machine learning system evaluates the retrieved user records to determine whether the user suffered a fall. If not, the method 900 continues to block 925, where the machine learning system labels the received sensor data. That is, the machine learning system can determine that the user did not fall (during the relevant window after the pressure data was recorded), and label the data accordingly. In some embodiments, as discussed above, the machine learning system may wait until defined criteria are met (e.g., a minimum period of time after the sensor data is recorded) before determining that a fall did not occur.

In at least one embodiment, in addition to determining whether the user fell, the machine learning system may determine whether the user stumbled. Though stumbles may generally be less dangerous than actual falls, they may nevertheless be indicative of potential concerns or problems. By labeling the data to predict stumbles, the system may be able to improve the overall results for the users.

If, at block 915, the machine learning system determines that a fall occurred, the method 900 continues to block 920. At block 920, the machine learning system determines one or more characteristics of the fall, such as the direction of the fall (e.g., forwards, backwards, or sideways), the location of the fall (e.g., the physical area in a facility), the severity of the fall (e.g., whether it resulted in lacerations, broken bone(s), sprains, etc.), and the like. In an embodiments, as discussed above, these characteristics are indicated in the user record(s) corresponding to the fall. In some embodiments, these characteristics are stored in a machine-readable format, such as using defined values or labels to indicate directionality and/or severity of the fall. In other embodiments, the machine learning system may evaluate written records (e.g., written by a caregiver at the time of the fall), such as by using natural language processing, to determine these fall characteristics.

The method 900 then continues to block 925, where the machine learning system labels the received sensor data to indicate the presence of the fall and/or the fall characteristics. As discussed above, this labeled data can then be used to train or refine one or more machine learning models to predict fall events. The method 900 then returns to block 905 to receive additional sensor data.

In this way, the machine learning system can automatically generate labeled training data. As discussed above, this process can significantly improve the accuracy and reliability of the resulting machine learning models, as well as significantly reduce the cost and inaccuracies involved in manually-labeling data.

Example Method for Training Machine Learning Models

Figure 10:
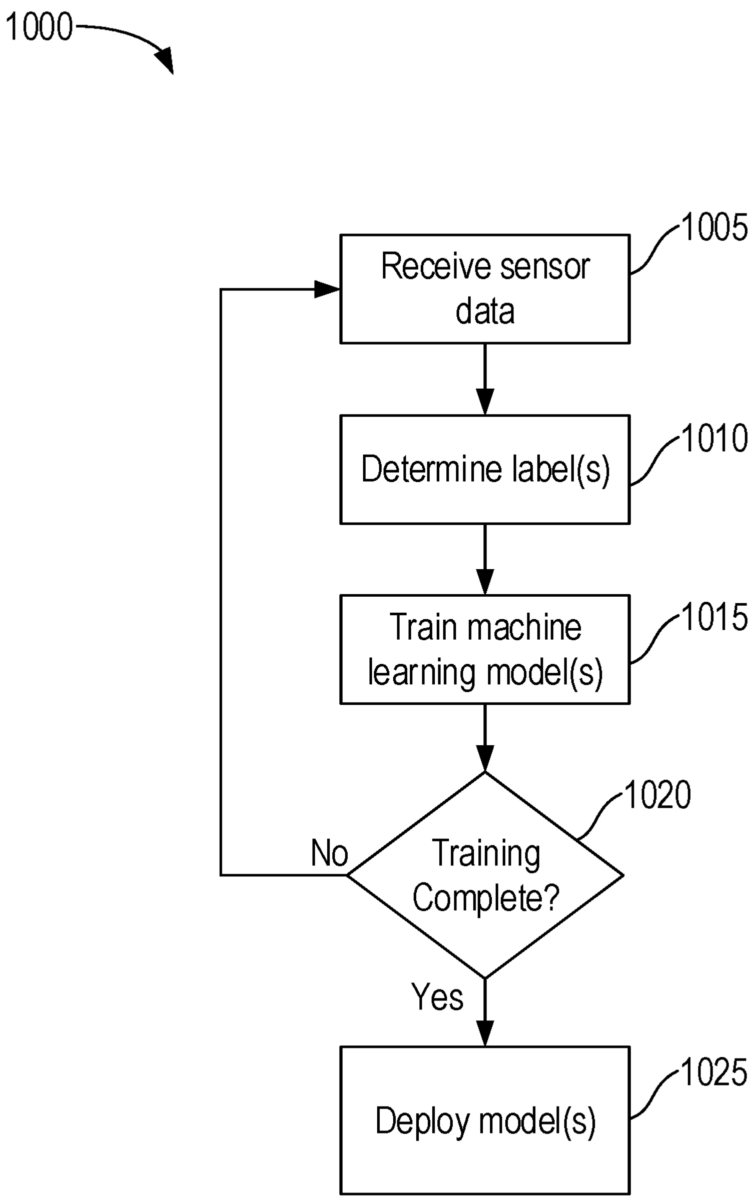
FIG. 10 is a flow diagram depicting an example method for training machine learning models based on sensor data to predict fall events.

FIG. 10 is a flow diagram depicting an example method 1000 for training machine learning models based on sensor data to predict fall events. In some embodiments, the method 1000 is performed by a machine learning system, such as machine learning system 515 of FIG. 5.

At block 1005, the machine learning system receives sensor data from one or more users. As discussed above, this sensor data can generally include a variety of data, such as the pressure exerted by the user's foot or feet at one or more points on the foot (or feet) while the user stands, walks, runs, and the like, motion data such as acceleration and movement of the foot (e.g., via an accelerometer on the ankle of the user), orientation data of the foot (e.g., via a gyroscope), blood pressure and/or pulse rate data of the user, and the like while the user stands, walks, runs, and the like. In some embodiments, as discussed above, the machine learning system can collect this data from a number of users (e.g., all patients in a long-term care facility) over a period of time (e.g., over the course of a year). In some embodiments, the machine learning system can further receive biographical data of each user, such as their age, weight, height, mobility issues, and the like.

At block 1010, the machine learning system determines a set of label(s) for the received data. For example, as discussed above, the machine learning system (or another system) may identify falls (e.g., recorded or reported in the user's patient data). The machine learning system (or other system) may then retrieve the corresponding sensor data records from one or more times prior to the fall, and label the data accordingly. For example, the machine learning system can retrieve records from a window of thirty seconds prior to the fall and label then as "fall imminent," retrieve the records beginning five minutes prior and label them as "fall upcoming," and so on.

In some embodiments, as discussed above, the machine learning system can additionally or alternatively label the records based on other characteristics of the fall, such as the direction of the fall, severity of the fall, and the like. Additionally, in some embodiments, if a sufficient period of time has elapsed without the user falling (e.g., if the record is more than a day old, more than a week old, and the like), the machine learning system can label these records as not indicative of an upcoming fall. One example of determining the sensor data labels is described above in more detail with reference to FIG. 9.

Once label(s) are determined, the method 1000 continues to block 1015, where the machine learning system trains one or more machine learning models based on the labeled data, as discussed above. Though the illustrated example depicts data collection, labeling, and training occurring sequentially for conceptual clarity, in some embodiments, the machine learning system may first collect and label data for some period of time, and move to model training after that period has elapsed (or after sufficient data has been collected).

In an embodiment, as discussed above, training the models generally includes providing the sensor data (as well as user characteristics or other patient data) as input to the model, and using the label to compute a loss (based on the generated output). In this way, the machine learning system can iteratively refine the model(s) based on the labeled data in order to improve their predictions.

At block 1020, the machine learning system determines whether training is complete. In embodiments, this determination may be made based on a variety of termination criteria. For example, the machine learning system may determine whether a defined number of training cycles have been completed, whether a minimum number of training records have been used, whether a defined period of time has elapsed while training, whether a minimum preferred accuracy has been met (e.g., determined using labeled data as test data), and the like. If training is not complete, the method 1000 returns to block 1005 to receive a new set of sensor data.

If training is complete, the method 1000 continues to block 1025, where the machine learning system deploys the trained model(s) for inferencing. As discussed above, this may include using the models locally (on the machine learning system) to process new data, providing the models to one or more other systems or devices to predict falls, and the like.

Figure 11:
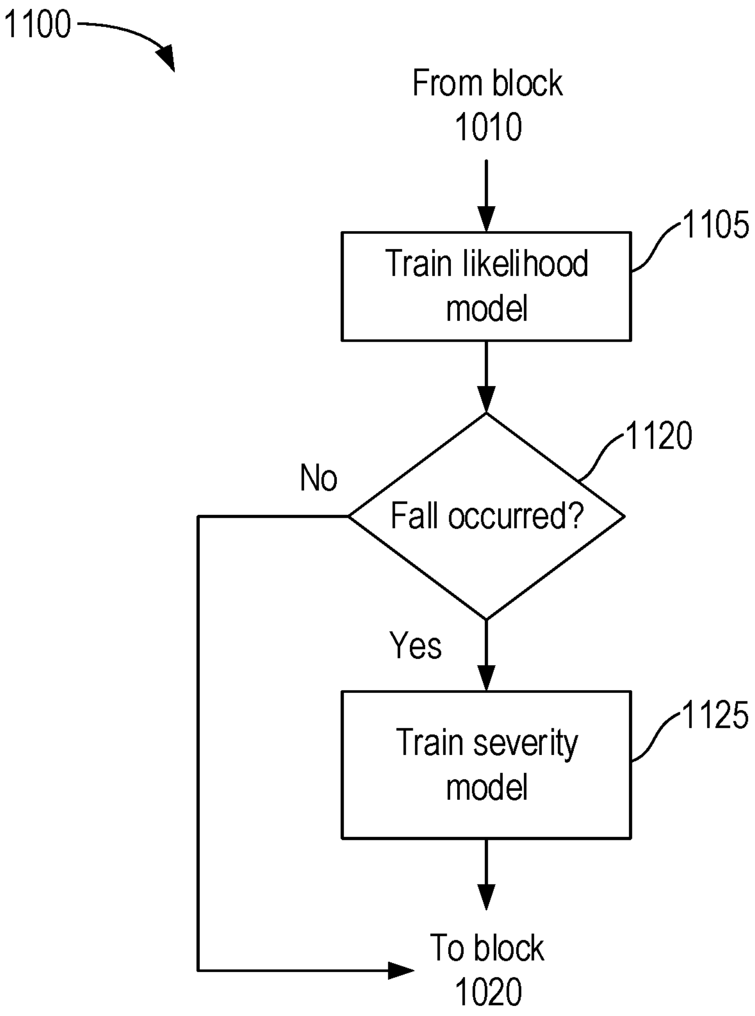
FIG. 11 is a flow diagram depicting an example method for training a likelihood model and a severity model to predict fall events.

Example Method for Training a Likelihood Model and a Severity Model to Predict Fall Events FIG. 11 is a flow diagram depicting an example method 1100 for training a likelihood model and a severity model to predict fall events. In some embodiments, the method 1100 is performed by a machine learning system, such as machine learning system 515 of FIG. 5. In the illustrated example, the method 1100 provides additional detail for block 1015 of FIG. 10.

At block 1105, the machine learning system trains a likelihood model based on the sensor data. In embodiments, the likelihood model is generally a machine learning model that learns to predict the likelihood of a user falling within some defined period. In some embodiments, the machine learning system predicts whether the user will fall within a fixed period. For example, a first model may predict imminent falls (e.g., within thirty seconds) while a second predicts upcoming falls (e.g., within a few hours or days), and so on. In at least one embodiment, a single model predicts both the likelihood or probability of a fall, as well as the expected time or delay until the fall.

In some embodiments, training the likelihood model includes processing the sensor data (and, in some embodiments, various user characteristics such as age and whether the user uses a cane, walker, or other assistive device) with the likelihood model in order to generate an output fall probability or prediction. This output can then be compared against the ground truth label for the sensor data (e.g., indicating whether a fall actually occurred, and if so, when). This comparison can be used to compute a loss (e.g., a cross-entropy loss) based on the difference(s) between the prediction and the label, and the loss may be used to refine the likelihood model (e.g., using backpropagation). Though stochastic gradient descent (e.g., refining the model individually for each individual exemplar) is described for conceptual clarity, in embodiments, the machine learning system may refine the likelihood model using batch gradient descent (based on a set of exemplars).

At block 1120, the machine learning system determines whether the label of the sensor data indicates that a fall occurred. If not, the method 1100 terminates, and returns to block 1020 of FIG. 10. That is, if the pressure data is not related to a fall, the machine learning system does not train or refine any other model(s), and the (negative) exemplar is used only to train the likelihood model.

If, at block 1120, the machine learning system determines that the data preceded a fall, the method 1100 continues to block 1125, where the machine learning system trains a severity model based on the data. Generally, the severity model is a machine learning model that learns to predict the severity of a fall for a given patient, presuming a fall will occur. In some embodiments, the machine learning system uses only user data (e.g., age, weight, height, assistive devices, and the like) to refine the severity model. In others, the machine learning system uses sensor data for the user, along with the user characteristics, to train the severity model.

For example, the severity model may be trained to receive the sensor data (and, in some embodiments, additional prior sensor data that may not have been used to train the likelihood model), along with one or more user characteristics, to generate a prediction as to how severe a fall would be, if one occurs. In some embodiments, this prediction includes consideration of the fall direction (e.g., forwards or backwards). In at least one embodiment, the severity model may be trained to predict which direction the user will fall, and this direction can be used to predict fall severity. In another embodiment, the fall direction can be implicitly learned internally by the model, and then used to predict the severity. That is, in some embodiments, the predicted severity is dependent on the predicted fall direction, regardless of whether the severity model itself outputs a predicted direction of the fall.

In an embodiment, in a similar manner to the likelihood model, the severity model can be trained by generating a predicted severity using the relevant input data, and comparing the predicted severity with a ground-truth severity (indicated by the label of the sensor data). This difference can be used to compute a loss, which may be used to refine the severity model (e.g., using stochastic gradient descent and/or batch gradient descent). The method 1100 then terminates and returns to block 1020 of FIG. 10.

Figure 12:
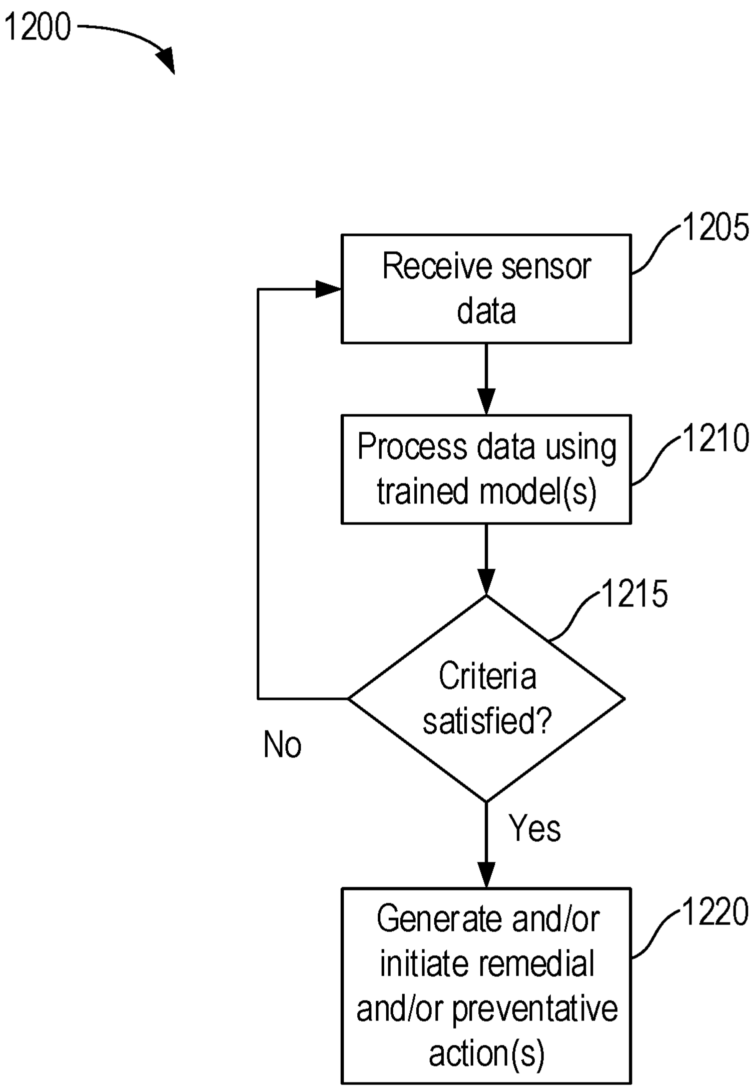
FIG. 12 is a flow diagram depicting an example method for using trained machine learning models to evaluate sensor data.

Example Method for Evaluating Sensor Data Using Trained Machine Learning Models FIG. 12 is a flow diagram depicting an example method 1200 for using trained machine learning models to evaluate sensor data. In some embodiments, the method 1200 is performed by a machine learning system, such as machine learning system 515 of FIG. 5. In some embodiments, the method 1200 is performed using the machine learning models trained using the method 1000 of FIG. 10.

At block 1205, the machine learning system receives sensor data. In an embodiment, as discussed above, this sensor data can generally include a variety of data, such as the pressure exerted by the user's foot or feet at one or more points on the foot (or feet) while the user stands, walks, runs, and the like, motion data such as acceleration and movement of the foot (e.g., via an accelerometer on the ankle of the user), orientation data of the foot (e.g., via a gyroscope), blood pressure and/or pulse rate data of the user, and the like while the user stands, walks, runs, and the like. In an embodiment, the sensor data received at block 1205 corresponds to data from a single user at a single point in time or over a window of time (e.g., over a thirty-second window). In some embodiments, the machine learning system can further receive biographical data of the user as discussed above, such as their age, weight, height, mobility issues, and the like.

At block 1210, the machine learning system processes the received data (which may include current sensor data as well as biographical data of the user) using one or more trained machine learning models, as discussed above. In some embodiments, this includes processing the data using all of the available models in parallel. For example, the machine learning system may use one model to predict whether a fall will occur imminently (e.g., within a defined (short) period of time), another model to predict whether a fall will occur in the future but not imminently, another model to predict the directionality and/or severity of the fall, and the like.

In some embodiments, as discussed above, the machine learning system may use these models sequentially, only using some models if the output from one or more prior model(s) meets defined criteria. For example, the machine learning system may only use the fall direction and/or severity model(s) if the fall occurrence model(s) indicate that a future fall is likely.

At block 1215, based on the generated prediction(s), the machine learning system determines whether one or more defined criteria are satisfied. In some embodiments, the criteria include determining whether a future fall is predicted with a sufficient level of confidence. In at least one embodiment, the criteria includes determining whether the predicted fall severity exceeds some defined thresholds (even if the fall likelihood does not). That is, the machine learning system may consider whether the fall would be particularly severe, even if the fall is not likely to occur. If the criteria are not satisfied, the method 1200 returns to block 1205 to receive new sensor data for evaluation. If one or more of the criteria are satisfied, the method 1200 continues to block 1220.

At block 1220, the machine learning system generates and/or initiates one or more remedial and/or preventative actions based on the generated predictions. For example, if the machine learning system determines that a fall is imminent, caregivers can be alerted and/or the patient can be instructed to sit or rest (e.g., by a caregiver and/or directly via the user's smartphone or other device). If the predictions indicate that a fall is likely in the next few hours or days, the machine learning system may prescribe medical devices such as canes or walkers. If the fall is predicted to be severe (even if unlikely), more forward-looking interventions may include instructions like added physical therapy for the user.

In at least one embodiment, the particular preventative actions selected may be determined based at least in part using the models themselves. For example, to determine whether to suggest a cane, walker, improved physical therapy, and the like, the machine learning system may modify one or more of the user's characteristics, and use this modified data as input to the model to determine whether the predicted fall risk or likelihood has decreased. This can enable the machine learning system to not only determine whether intervention is needed, but also to identify the best intervention that is most likely to reduce the fall risk (or fall severity). One example of this predictive process is discussed below in more detail with reference to FIG. 16.

In at least one embodiment, as discussed above, the machine learning system can also aggregate predicted falls and/or severities to provide facility-wide suggestions, such as to identify potential hazards like cords in a walkway, uneven ground, and the like. These suggestions can be used to improve the facility overall.

Figure 13:
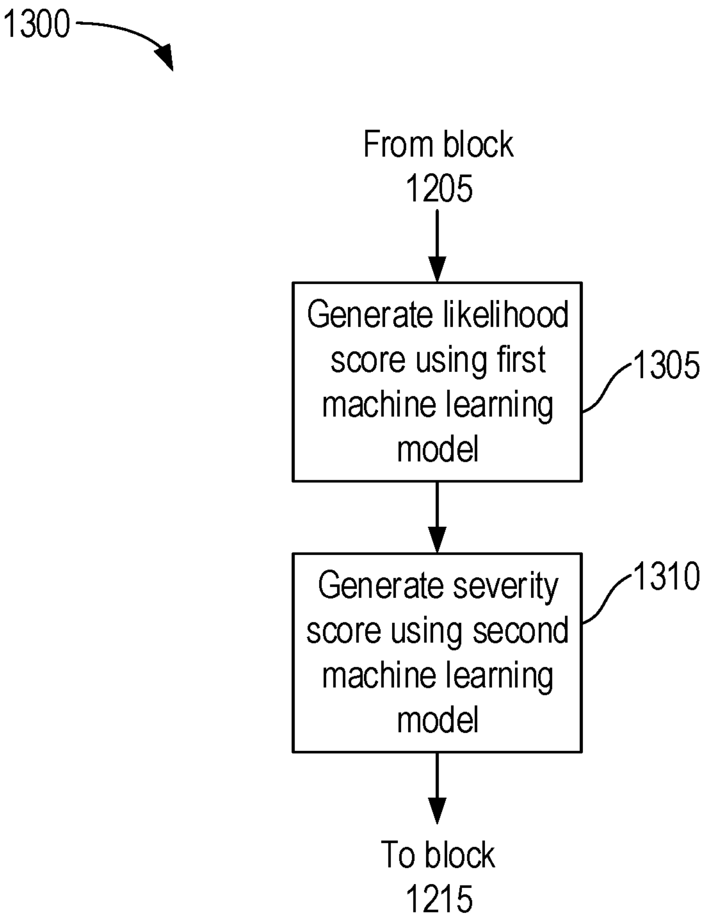
FIG. 13 is a flow diagram depicting an example method for predicting fall risk and potential severity using machine learning models.

Example Method for Predicting Fall Risk and Severity Using Machine Learning Models FIG. 13 is a flow diagram depicting an example method 1300 for predicting fall risk and potential severity using machine learning models. In some embodiments, the method 1300 is performed by a machine learning system, such as machine learning system 515 of FIG. 5. In some embodiments, the method 1300 provides additional detail for block 1210 of FIG. 12.

At block 1305, the machine learning system generates a fall likelihood score by processing the user data (which may include sensor data, as well as biographical data) using a first machine learning model. In an embodiment, the likelihood score indicates a probability or likelihood that the user will suffer a fall at some point in the future. Depending on the particular implementation, the timeline of this prediction may vary. For example, the first model may be trained to predict whether a fall is likely within the next five minutes or five days. In some embodiments, rather than a single model to generate the likelihood score, the machine learning system uses a set of models, each configured to predict fall likelihood over a corresponding window of future time.

In some embodiments, as discussed above, the machine learning system may selectively use these models depending on the output of the prior models. For example, the machine learning system may use a model that predicts falls over a five minute window only if a model predicting falls in the next thirty seconds does not indicate that a fall is likely. Similarly, the machine learning system may only use a model that predicts falls over the next five hours only if the five-minute model does not indicate that a fall is likely.

At block 1310, the machine learning system generates a severity score by processing the user data (e.g., sensor data and biographical data) using a second machine learning model. In an embodiment, the severity score indicates a probable, likely, or possible severity of a future fall (e.g., in terms of the types of injuries that are likely, the severity or intensity of those injuries, and the like). In some embodiments, the severity is based in part on a predicted fall direction (which may be predicted using a separate model, or using the second machine learning model). Similarly, as the models include user data such as age, weight, and height as input, they inherently learn to adjust the predicted severity based on these contributing factors.

In some embodiments, as discussed above, the machine learning system may selectively use this severity model depending on the output of the risk model(s). For example, if the likelihood model(s) do not indicate that a fall is likely, the machine learning system may refrain from using the severity model in order to reduce computational expense and latency. Similarly, in one embodiment, if the likelihood model(s) indicate that a fall is imminent (e.g., within thirty seconds), the machine learning system may refrain from using the severity model(s). In contrast, if the likelihood model(s) predict that a fall is likely, but not imminent, the machine learning system can use the severity model(s) to enable improved selection of the available targeted interventions. Further, in some embodiments the machine learning system may use the severity model regardless of the output of the likelihood model(s) (e.g., to allow for interventions with users that, though generally stable, could suffer catastrophic injury in the event of a fall). Additionally, in at least one embodiment, the likelihood model(s) and severity model(s) may collectively be referred to as fall risk models.

Figure 14:
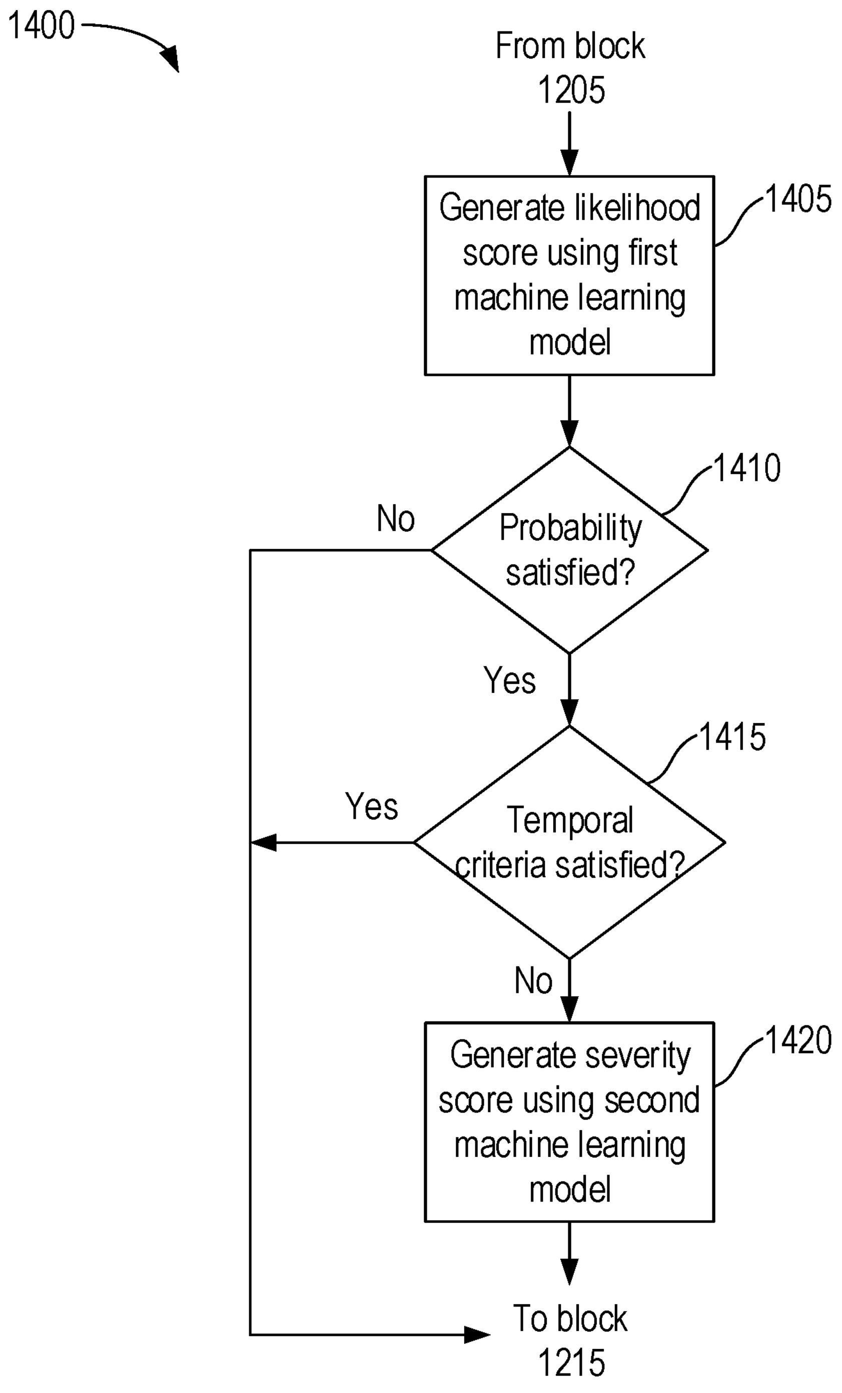
FIG. 14 is a flow diagram depicting an example method for predicting fall events and severity using machine learning.

Example Method for Predicting Fall Events and Severity Using Machine Learning FIG. 14 is a flow diagram depicting an example method 1400 for predicting fall events and severity using machine learning. In some embodiments, the method 1400 is performed by a machine learning system, such as machine learning system 515 of FIG. 5. In the illustrated example, the method 1400 provides additional detail for block 1210 of FIG. 12. In one embodiment, the method 1400 differs from the method 1300 in that, using the method 1400, the machine learning system can determine whether to apply various models based on the output of prior models.

At block 1405, the machine learning system generates a likelihood score for the user using a first machine learning model. For example, as discussed above, the machine learning system may process the user's sensor data (e.g., from a thirty second window) and/or the user's characteristics or biographical data using one or more likelihood models to determine whether there is a likelihood that the user will fall at some point in the future (e.g., within one or more defined windows of time).

At block 1410, the machine learning system determines whether the predicted fall probability or likelihood satisfies some defined threshold. For example, the machine learning system may determine whether a fall is predicted to occur, the generated confidence in the possible future fall, and the like. If the probability criteria are not satisfied, the method 1400 terminates and returns to block 1215 (where the machine learning system will likely determine that the criteria are not satisfied, and no interventions should be initiated).

If, at block 1410, the fall probability criteria are satisfied, the method 1400 continues to block 1415, where the machine learning system determines whether one or more temporal criteria are satisfied. In some embodiments, these temporal criteria relate to the urgency of the potential fall (e.g., how imminently or soon it is predicted to occur). For example, if the fall is predicted to occur within some defined "imminent" timeframe (e.g., within seconds or minutes), the machine learning system may determine that the temporal criteria are satisfied, and therefore bypass use of the severity model.

That is, if a fall is predicted to occur imminently, the machine learning system may determine that processing data using the severity model is useless, as the fall is likely to occur before the predicted severity is relevant. For example, if the user is expected to fall in the next few seconds or minutes, the potential severity of the fall may generally be irrelevant to the appropriate intervention: immediate response by one or more caregivers. By refraining from using the severity model, therefore, the machine learning system can save significant computational resources that need not be spent.

If, at block 1415, the machine learning system determines that the temporal criteria are not satisfied (e.g., because the fall is predicted to occur over the next few hours or days, rather than immediately), the method 1400 continues to block 1420, where the machine learning system generates a severity score using a second trained machine learning model. As discussed above, this severity score can generally indicate the likely severity of any future falls, such as whether they may result in broken bone(s) (and if so, which bone(s)), lacerations, or other complications. In an embodiment, the potential severity may be an important factor in selecting appropriate interventions and performing other actions.

Figure 15:
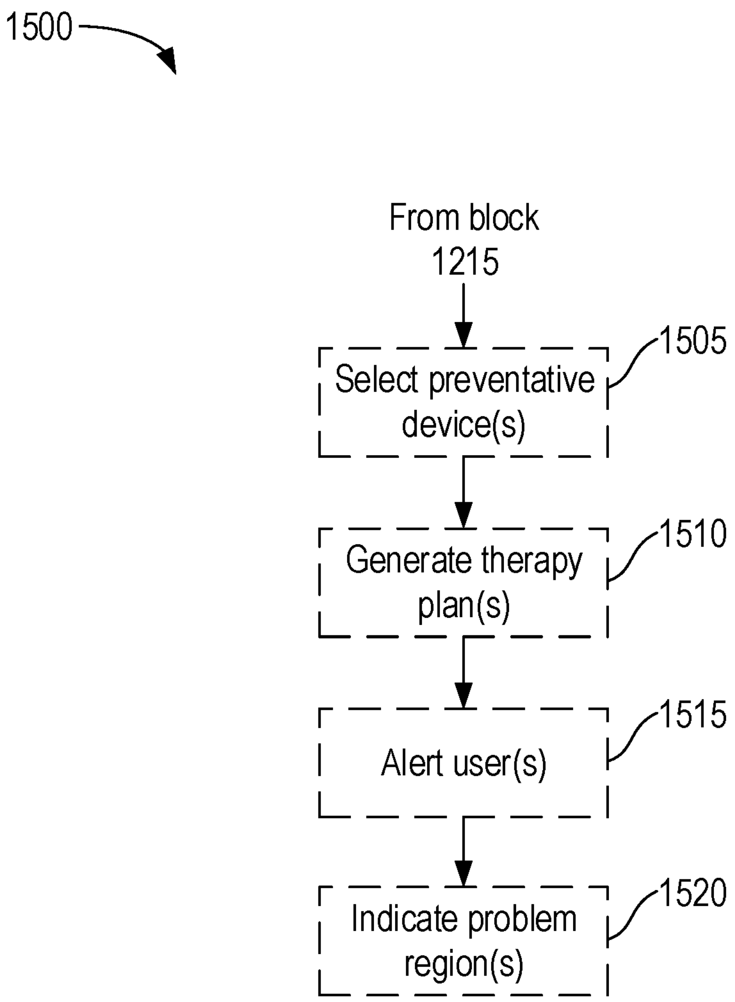
FIG. 15 is a flow diagram depicting an example method for initiating preventative and/or remedial actions based on machine learning model output.

Example Method for Initiating Preventative and Remedial Actions Based on Machine Learning Models FIG. 15 is a flow diagram depicting an example method 1500 for initiating preventative and/or remedial actions based on machine learning model output. In some embodiments, the method 1500 is performed by a machine learning system, such as machine learning system 515 of FIG. 5. In some embodiments, the method 1500 provides additional detail for block 1220 of FIG. 12.

The method 1500 generally indicates a variety of optional interventions that can be selected and implemented by the machine learning system, depending on the particular implementation, as well as on the particular likelihood score(s) and/or severity score(s) that are generated.

At block 1505, the machine learning system can optionally select one or more assistive or preventative devices for the user. For example, the machine learning system may suggest a cane, a walker, a wheelchair, a mobility scooter, and the like. This selection may be determined using machine learning (e.g., by processing modified user data with the models, as discussed above), using a rules-based system (e.g., based on the user's age, weight, mobility status, and the like), and the like. In some embodiments, the machine learning system can further consider the potential severity score to determine the best preventative device. For example, if the predicted fall severity is below a threshold, the machine learning system may indicate that the user can try a cane to retain mobility without significant inconvenience. If the severity is above some threshold, however, the machine learning system may indicate that a mobility scooter should be used, because the harm from a potential fall (even with other devices such as a cane) could be significant.

At block 1510, the machine learning system can optionally generate one or more therapy plans for the user. For example, as discussed above, if the machine learning system predicts that the user will fall towards one side, the machine learning system can suggest therapies or exercises that will improve the user's strength on this side and thereby reduce the chance of a fall in that direction. Similarly, if the fall severity is predicted to exceed some threshold, additional physical therapy may be useful to help reduce the likely harm from the fall. In embodiments, as discussed above, the particular therapy may be selected using machine learning (e.g., by processing modified sensor data or user data using the models), a set of defined rules (e.g., instructing strength training on one side when the fall is likely to be towards that side), and the like.

At block 1515, the machine learning system optionally alerts one or more user(s) of the upcoming potential fall. This may include, for example, alerting the user that they may be about to suffer a fall (e.g., via a smartphone of the user, via one or more output devices in the vicinity, such as smart televisions or speakers, and the like). For example, the machine learning system may suggest that the user grasp an object for support, sit down, slow down, and the like. In some embodiments, the alerts can be provided to one or more caregivers (e.g., to caregivers responsible for the user, or to caregivers identified as being nearby, physically, to the user). This alert may indicate a variety of data depending on the generated risk and/or severity scores. For example, the alert may indicate an urgency of the risk (e.g., how quickly the user needs to respond, and/or how severe the fall may be).

At block 1520, the machine learning system can optionally indicate problem region(s) in the space. For example, as discussed above, in some embodiments the machine learning system can aggregate predicted falls across users and/or time to identify physical regions of the facility that are particularly risky (e.g., using a heat map of user locations at the time of the predicted or actual falls). These locations may include hazards that can or should be mitigated, as discussed above.

Generally, each of the possible interventions in the method 1500 are optional, and the actual interventions initiated by the machine learning system may vary according to a wide variety of concerns and implementation details.

Figure 16:
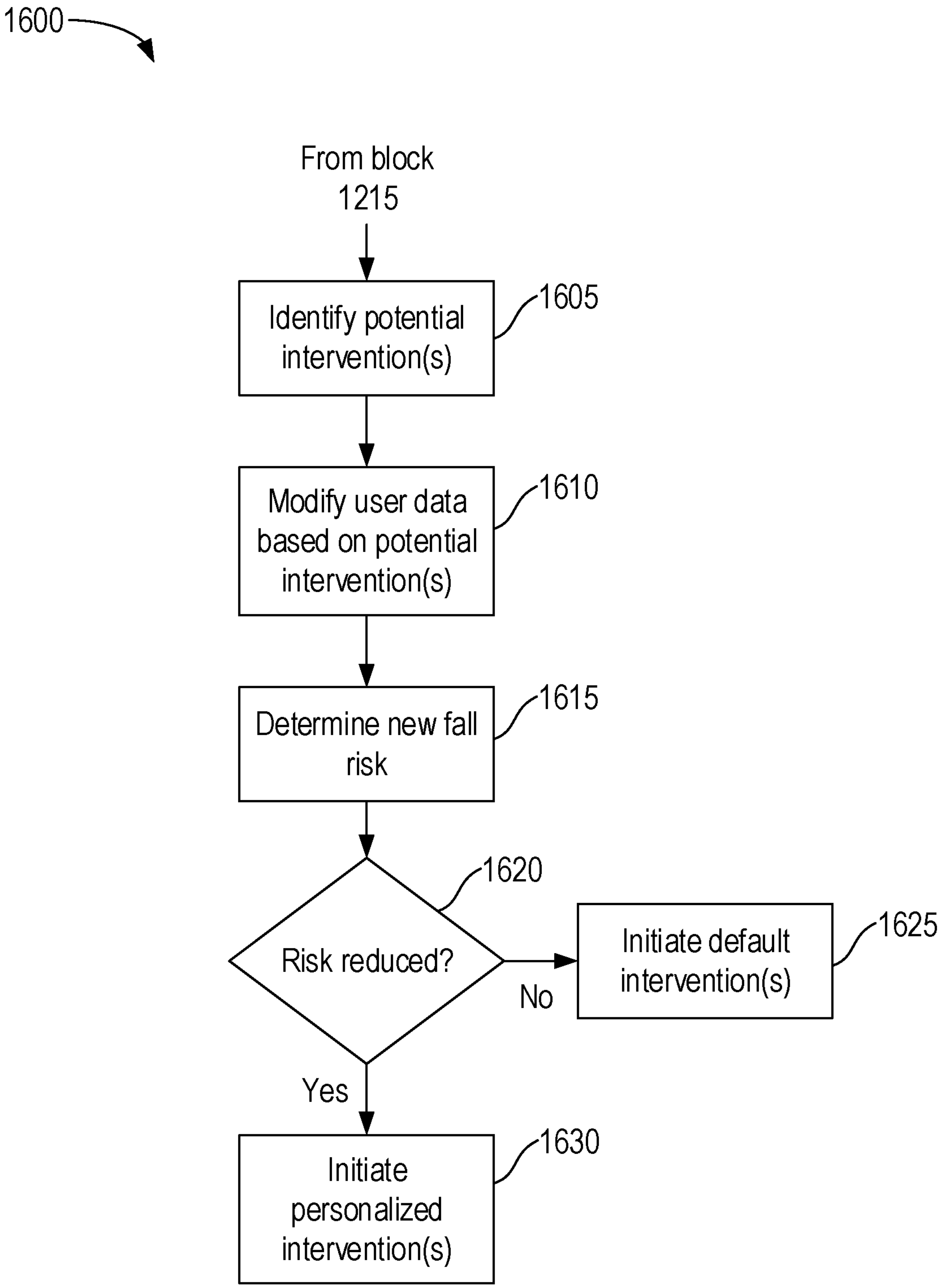
FIG. 16 is a flow diagram depicting an example method for evaluating and selecting personalized interventions using machine learning.

Example Method for Evaluating and Selecting Personalized Interventions Using Machine Learning FIG. 16 is a flow diagram depicting an example method 1600 for evaluating and selecting personalized interventions using machine learning. In some embodiments, the method 1600 is performed by a machine learning system, such as machine learning system 515 of FIG. 5. In the illustrated example, the method 1600 provides additional detail for block 1220 of FIG. 12 (after the machine learning system determines that a fall is likely, and decides to initiate one or more interventions).

At block 1605, the machine learning system identifies a set of potential intervention(s) for the user. For example, as discussed above with reference to FIG. 15, the machine learning system may select various assistive or preventative medical devices (such as a cane or walker), generate a new or revised therapy plan, alert nearby user(s), and the like. In some embodiments, the potential interventions are selected based at least in part on the user's current characteristics. For example, if the user does not currently use any assistive device, the machine learning system may select one or more to suggest. If the user uses a device such as a cane, the machine learning system may suggest a more robust device such as a walker. In some embodiments, the machine learning system may determine whether the user has assistance standing up and/or walking, and suggest such assistance.

At block 1610, the machine learning system modifies the user data based on the potential interventions. That is, the machine learning system may artificially adjust the user data to reflect at least one of the proposed interventions. At block 1615, the machine learning system determines a revised fall risk for the user, based on this modified user data. As discussed above, the fall risk may generally correspond to the likelihood of a fall and/or the severity of a potential fall.

For example, if the user does not use a cane, the machine learning system may reprocess the user's data (and pressure data, in some aspects), indicating that the user does have a cane, using the machine learning model(s). This can allow the machine learning system to simulate the effect of various interventions. At least one embodiment, the machine learning system repeats blocks 1610 and 1615 for each of the potential interventions determined in block 1605. That is, the machine learning system can separately determine revised fall risks for each possible intervention (and, in some embodiments, for combinations of interventions).

At block 1620, the machine learning system determines whether the potential intervention(s) reduced the fall risk, as compared to the user's unmodified data. If not, the method 1600 continues to block 1625, where the machine learning system initiates one or more default interventions. For example, even if the simulation does not indicate that a walker would reduce the fall risk, the machine learning system may nevertheless assign, provide, or facilitate provision of a walker for the user.

If, at block 1620, the machine learning system determines that one or more potential intervention(s) would reduce the fall risk, the method 1600 continues to block 1630, where the machine learning system initiates one or more of these personalized interventions. As these interventions are specifically designed for the particular user, and are validated via one or more simulations using machine learning, they may be better able to reduce the risk to the user and improve the overall results.

Example Method for Determining Aggregated Fall Risks Using Machine Learning

Figure 17:
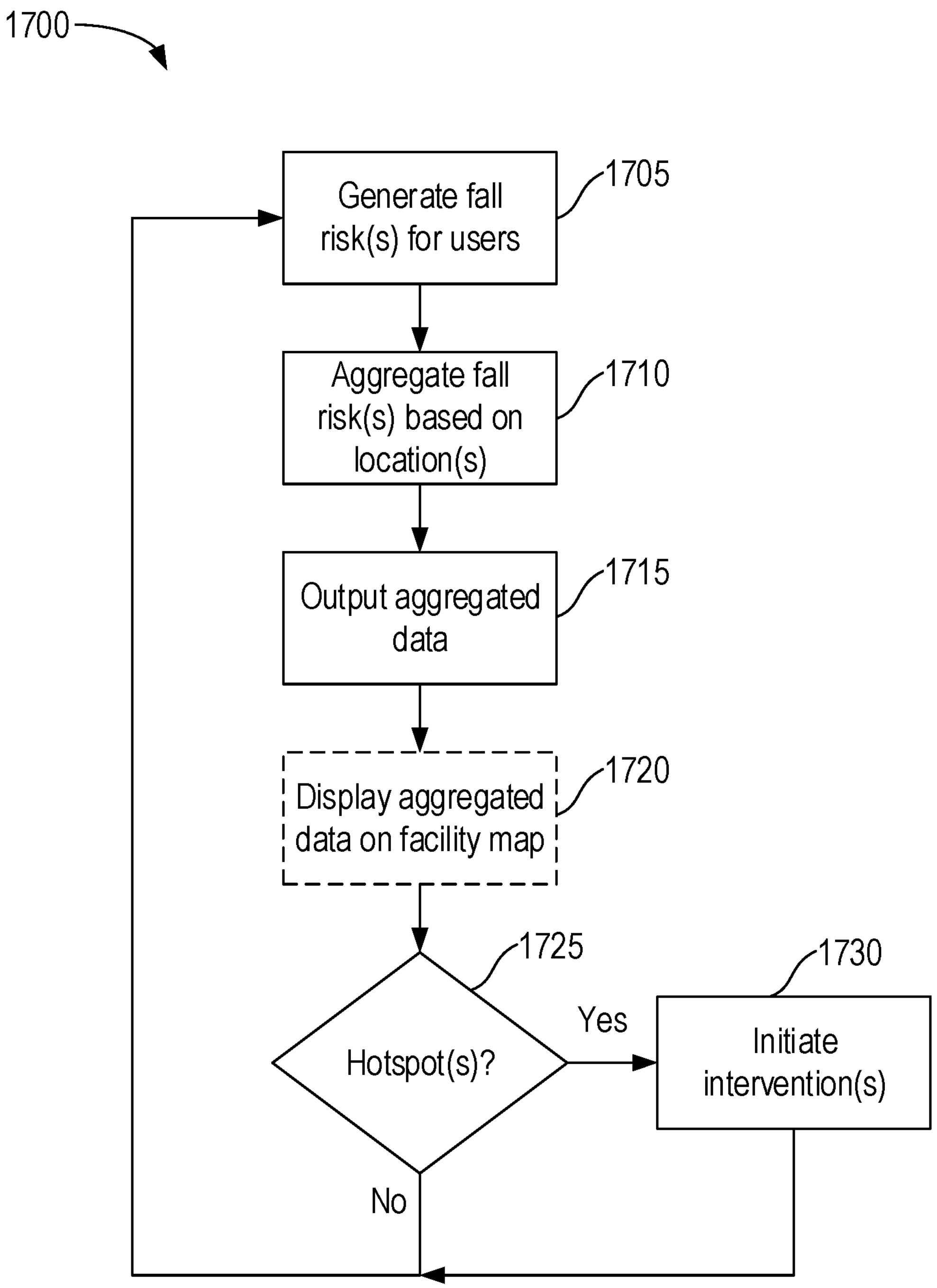
FIG. 17 is a flow diagram depicting an example method for determining aggregated fall risks using machine learning.

FIG. 17 is a flow diagram depicting an example method 1700 for determining aggregated fall risks using machine learning. In some embodiments, the method 1700 is performed by a machine learning system, such as machine learning system 515 of FIG. 5.

At block 1705, the machine learning system generates a set of fall risk scores for a set of users. As discussed above, the fall risk score can generally quantify, for each user, the likelihood of a fall in the future and/or the potential severity of such a fall. In embodiments, the machine learning system can generate the fall risk score(s) for each user by processing data associated with each user (e.g., sensor data from wearable devices and/or user characteristics) using one or more trained machine learning models, as discussed above.

In some embodiments, the machine learning system may generate multiple risk scores for each user, based in part on when the sensor data is collected. That is, the machine learning system may generate risk scores for a single user at multiple points in time, where the score at each point is based on sensor data from the user at or near that time. For example, the machine learning system may generate a first score at a first time (e.g., at noon) based on sensor data from one or more windows prior to noon, and generate a second score at a second time (e.g., at three in the afternoon) based on sensor data from windows prior to three in the afternoon.

At block 1710, the machine learning system aggregates the generated fall risks based on the location(s), in the facility, where user was when the pressure data used to generate the risk score was collected. That is, for each generated fall risk score, the machine learning system can identify the physical location(s) of the user when the sensor data was collected, and aggregate the scores based on these locations. For example, the machine learning system may, for one or more physical spaces or locations in the facility, identify a set of risk scores that are associated with each location (e.g., where the sensor data was collected within a defined distance from the location).

In some embodiments, this aggregation includes determining a number of likely falls in each space (e.g., the number of times the machine learning system predicted a fall with sufficient probability), determining a potential severity of falls in each space (e.g., the average or maximum predicted severity, among the risk scores), and the like.

At block 1715, the outputs the aggregated data. For example, the machine learning system may provide a textual summary of the aggregated risks (e.g., indicating the number of predicted falls, the predicted severity, identifying users and/or regions with a large number of predicted falls, and the like).

At block 1720, the machine learning system can optionally display the aggregated data on a facility map. For example, as discussed above with reference to FIG. 8, the machine learning system may generate and output a heat map showing the distribution of fall probabilities, fall severities, or a combination of the two. Such an augmented floorplan or map can be particularly useful to help users quickly identify problematic or hazardous areas.

At block 1725, the machine learning system determines whether there are any hotspots in the facility. That is, the machine learning system can determine whether any of the locations or spaces satisfy one or more defined criteria relating to the number and/or frequency of predicted falls, the potential severity of falls, and the like. If no such hotspots are found, the method 1700 returns to block 1705.

If at least one hotspot is identified, the method 1700 continues to block 1730, where the machine learning system initiates one or more interventions. For example, as discussed above, the machine learning system may indicate the location to one or more users or caregivers, and instruct that they investigate the area to identify potential hazards. In some embodiments, if a hotspot is identified in a private or semi-private area (e.g., a user's private room), the machine learning system can identify the user (or users) associated with that space, in order to enable more targeted interventions with these user(s). The method 1700 then returns to block 1705.

Example Method for Predicting Falls Using Wearable Devices

Figure 18:
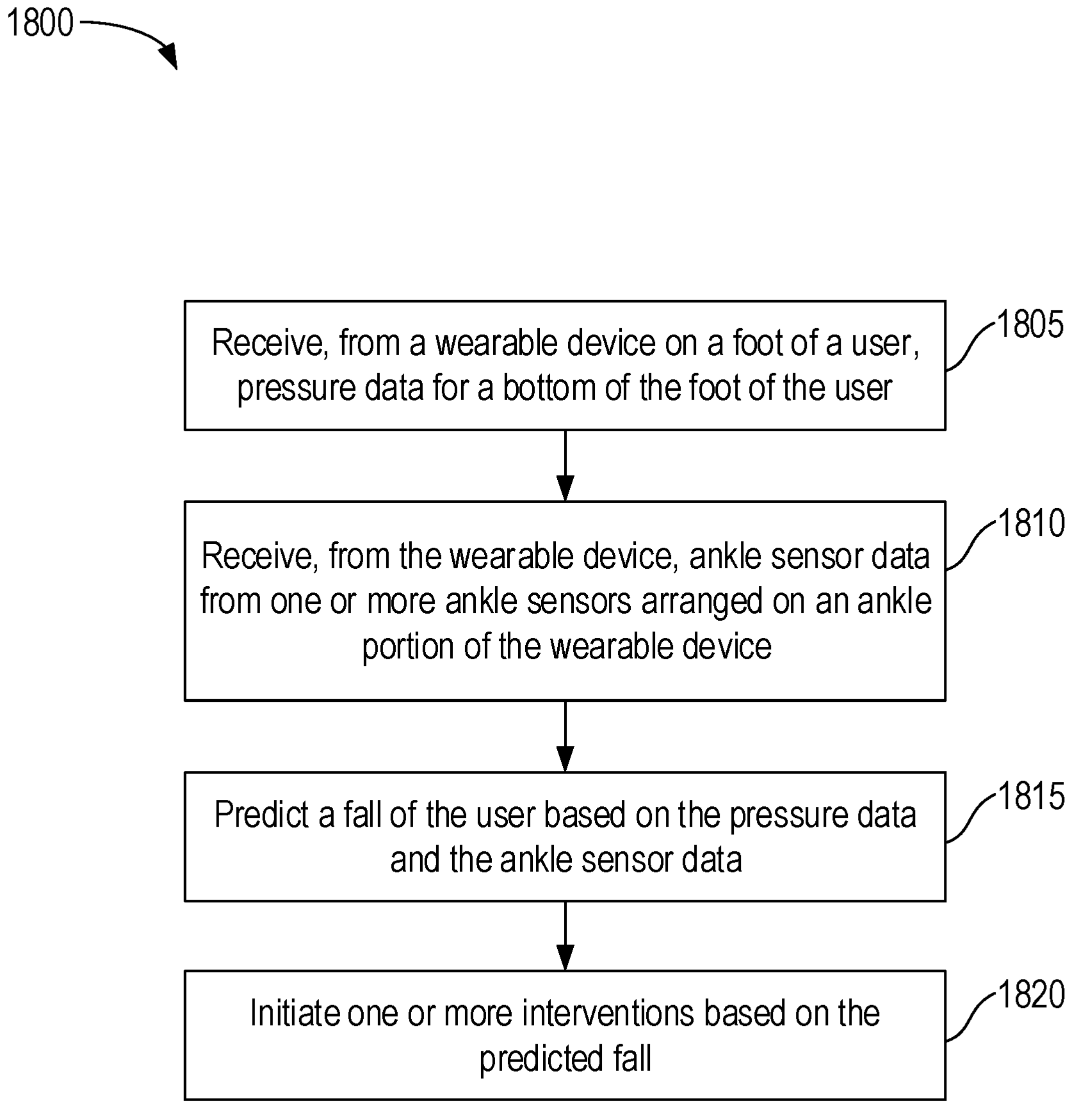
FIG. 18 is a flow diagram depicting an example method for predicting falls using wearable devices.

FIG. 18 is a flow diagram depicting an example method for predicting falls using wearable devices. In some embodiments, the method 1800 is performed by a machine learning system, such as machine learning system 515 of FIG. 5.

At block 1805, pressure data for a bottom of a foot of a user is received from a wearable device on the foot of the user. For example, as discussed above, a wearable device 105 (such as the smart sock discussed in reference to FIG. 1A and/or a smart shoe discussed in reference to FIG. 1B) may be used to collect and provide the sensor data from one or more pressure sensors on the user's foot.

At block 1810, ankle sensor data from one or more ankle sensors arranged on an ankle portion of the wearable device are received from the wearable device. For example, as discussed above, the ankle sensors may include an accelerometer, a gyroscope, a blood pressure sensor, and the like. In some aspects, the ankle sensors are included in a removable component detachably attached to the ankle of the wearable device.

At block 1815, a fall of the user is predicted based on the pressure data and the ankle sensor data. For example, as discussed above, the machine learning system may process the sensor data using one or more machine learning models to predict fall likelihood, fall severity, and the like.

At block 1820, one or more interventions are initiated based on the predicted fall. For example, as discussed above, the system may alert the user and/or a caregiver, prescribe additional assistance, and the like.

Example Wearable Device for Improved Fall Detection and Prevention

Figure 19:
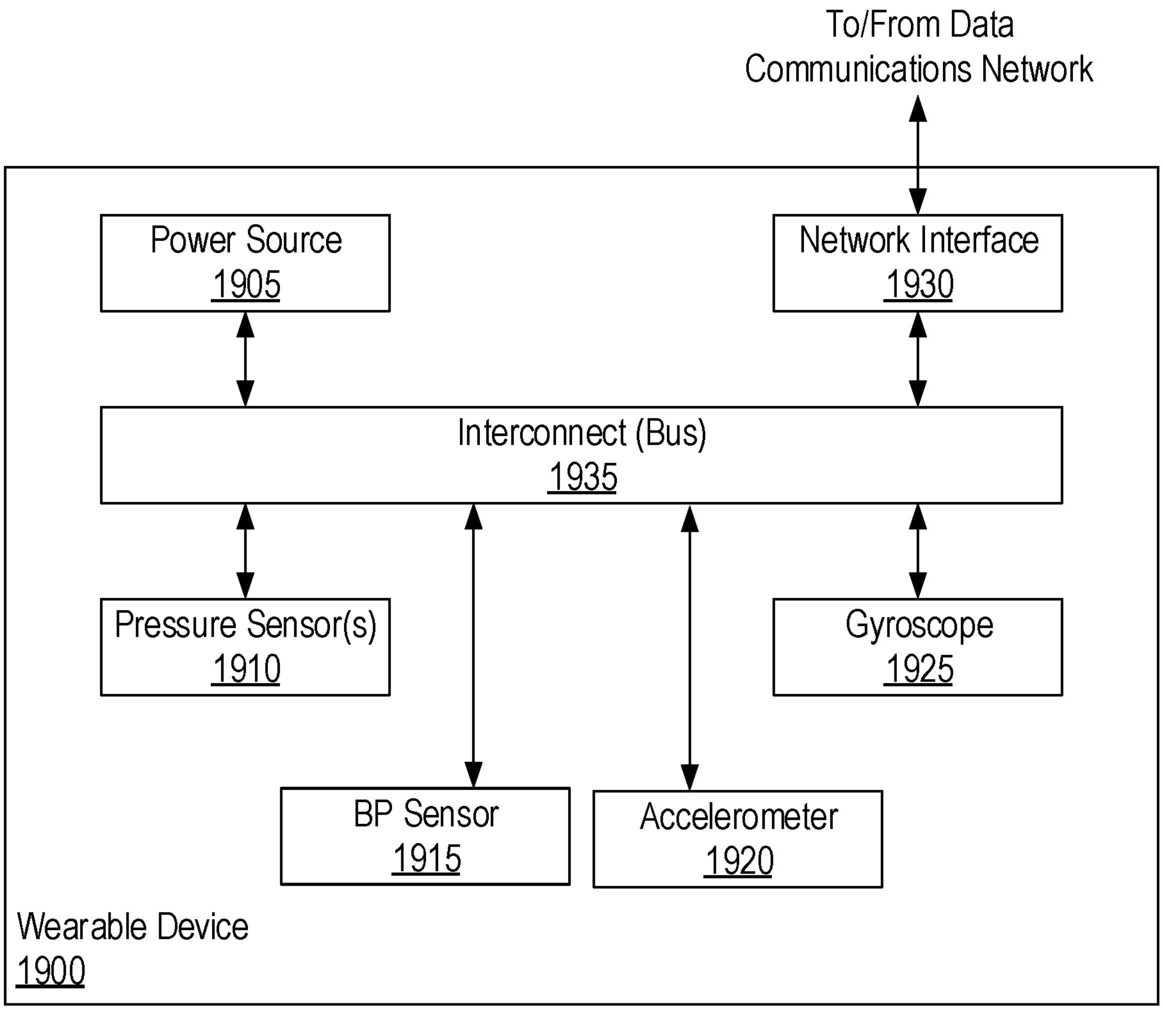
FIG. 19 depicts an example wearable device configured to perform various aspects of the present disclosure.

FIG. 19 depicts an example wearable device 1900 configured to perform various aspects of the present disclosure. In one embodiment, the wearable device 1900 corresponds to the wearable device 105A of FIG. 1A, the wearable device 105B of FIG. 1B, the wearable device 105 of FIG. 2, the wearable device 105 of FIG. 3, the ankle unit 305 of FIG. 3, and the like.

As illustrated, the wearable device 1900 includes a power source 1905 (e.g., power source 460 of FIG. 4), one or more pressure sensors 1910 (e.g., pressure sensors 110 of FIGS. 1A, 1B and/or pressure sensors 210 of FIG. 2), one or more blood pressure sensors 1915 (e.g., an ankle sensor 115 of FIGS. 1A, 1B and/or 4), one or more accelerometers 1920 (e.g., an ankle sensor 115 of FIGS. 1A, 1B and/or 4), one or more gyroscopes 1925 (e.g., an ankle sensor 115 of FIGS. 1A, 1B and/or 4), and one or more network interfaces 1930 (e.g., a transmitter 455, port 465, and/or port 470 of FIG. 4). As illustrated, the power source 1905, pressure sensors 1910, blood pressure sensors 1915, accelerometers 190, gyroscope 1925, and network interface 1930 are communicatively coupled by one or more buses 1935.

As discussed above, via the network interface 1930, the wearable device 1900 can be communicatively coupled with one or more other devices and components (e.g., directly via a cable or wire, via a network, which may include the Internet, local network(s), and the like) such as user devices (e.g., smartphones), remote servers (e.g., machine learning systems), pressure sensors, and the like.

Though not depicted in the illustrated example, in some embodiments, some or all of the wearable device 1900 may be included within a detachable or removable unit, such as the ankle unit 305 of FIGS. 3 and 4. Additionally, though not depicted in the illustrated example, in some embodiments, the wearable device 1900 can additionally or alternatively include other sensors, such as pulse sensors, oxygen sensors, and the like.

Though not depicted in the illustrated example, in some embodiments, the wearable device 1900 may also include one or more other computing components as needed, such as a CPU configured to retrieve and execute programming instructions stored in memory as well as store and retrieve application data residing in storage (which may include single CPU and/or GPU, multiple CPUs and/or GPUs, a single CPU and/or GPU having multiple processing cores), a memory (which may be a random access memory), a storage (which may be any combination of disk drives, flash-based storage devices, and the like, and may include fixed and/or removable storage devices, such as fixed disk drives, removable memory cards, caches, optical storage, network attached storage (NAS), or storage area networks (SAN)), one or more I/O interfaces (to enable input or output such as via buttons, lights, audio, and the like), and the like.

Example Processing System for Improved Machine Learning Models

Figure 20:
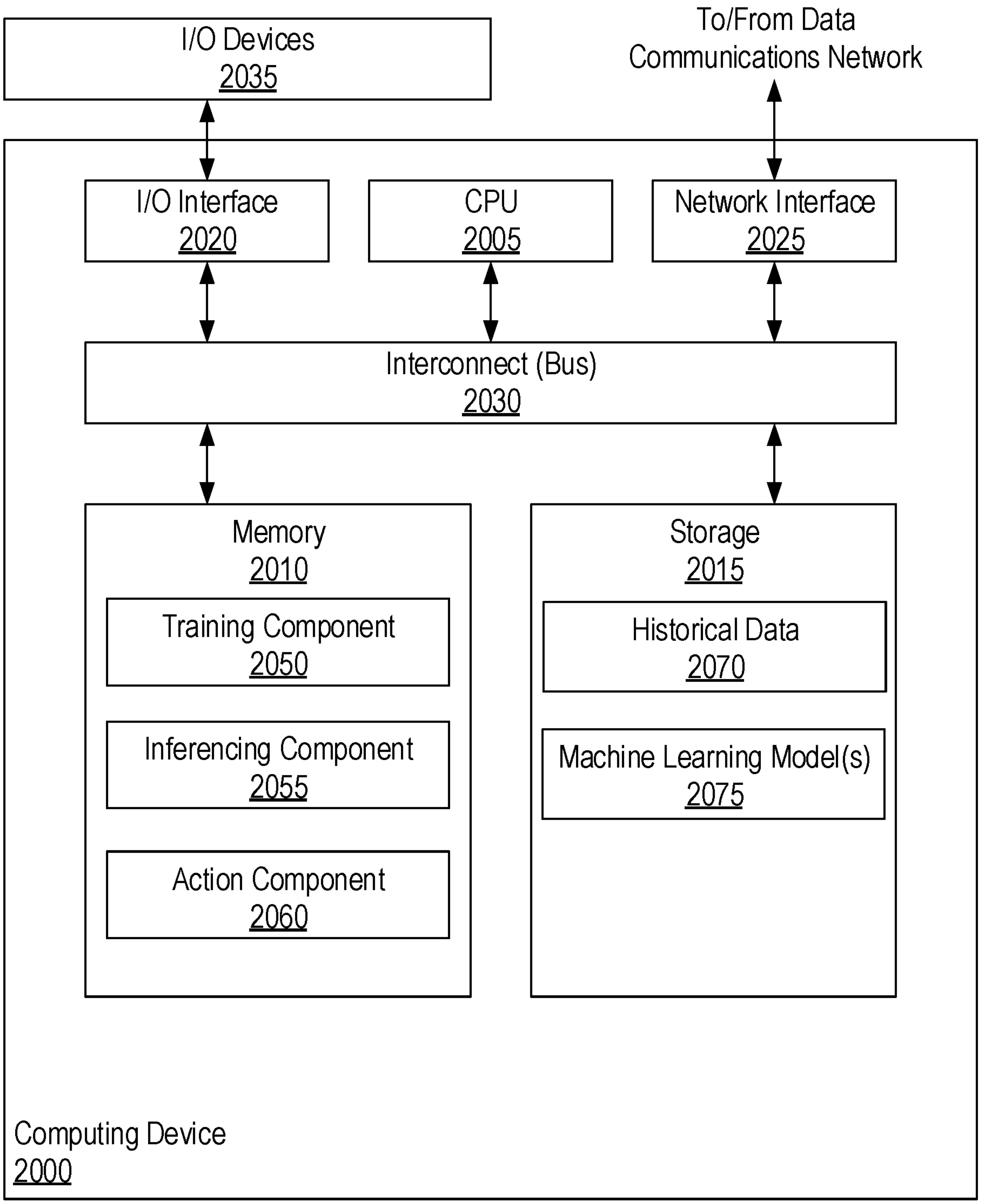
FIG. 20 depicts an example computing device configured to perform various aspects of the present disclosure.

FIG. 20 depicts an example computing device 2000 configured to perform various aspects of the present disclosure. Although depicted as a physical device, in embodiments, the computing device 2000 may be implemented using virtual device(s), and/or across a number of devices (e.g., in a cloud environment). In one embodiment, the computing device 2000 corresponds to the machine learning system 515 of FIG. 5.

As illustrated, the computing device 2000 includes a CPU 2005, memory 2010, storage 2015, a network interface 2025, and one or more I/O interfaces 2020. In the illustrated embodiment, the CPU 2005 retrieves and executes programming instructions stored in memory 2010, as well as stores and retrieves application data residing in storage 2015. The CPU 2005 is generally representative of a single CPU and/or GPU, multiple CPUs and/or GPUs, a single CPU and/or GPU having multiple processing cores, and the like. The memory 2010 is generally included to be representative of a random access memory. Storage 2015 may be any combination of disk drives, flash-based storage devices, and the like, and may include fixed and/or removable storage devices, such as fixed disk drives, removable memory cards, caches, optical storage, network attached storage (NAS), or storage area networks (SAN).

In some embodiments, I/O devices 2035 (such as keyboards, monitors, etc.) are connected via the I/O interface(s) 2020. Further, via the network interface 2025, the computing device 2000 can be communicatively coupled with one or more other devices and components (e.g., via a network, which may include the Internet, local network(s), and the like). As illustrated, the CPU 2005, memory 2010, storage 2015, network interface(s) 2025, and I/O interface(s) 2020 are communicatively coupled by one or more buses 2030.

In the illustrated embodiment, the memory 2010 includes a training component 2050, an inferencing component 2055, an action component 2060, which may perform one or more embodiments discussed above. Although depicted as discrete components for conceptual clarity, in embodiments, the operations of the depicted components (and others not illustrated) may be combined or distributed across any number of components. Further, although depicted as software residing in memory 2010, in embodiments, the operations of the depicted components (and others not illustrated) may be implemented using hardware, software, or a combination of hardware and software. In one embodiment, the training component 2050 is used to train the machine learning model(s), such as by using the method 1000 of FIG. 10, the inferencing component 2055 may be configured to use the models to predict falls and/or severity using trained models, such as by using the method 1200 of FIG. 12, and the action component 2060 may be configured to generate and/or initiate various responsive actions to the risks, such as by using the method 1500 of FIG. 15.

In the illustrated example, the storage 2015 includes historical data 2070 (which may correspond to labeled sensor data and/or user data used to train and/or evaluate the models), as well as one or more machine learning model(s) 2075. Although depicted as residing in storage 2015, the historical data 2070 and machine learning model(s) 2075 may be stored in any suitable location, including memory 2010. Generally, the historical data 2070 includes the previously-received (and labeled) sensor data, as well as any relevant user data (e.g., user age and weight data) used to train the machine learning models 2075.

Example Clauses

Clause 1: A smart sock, comprising: one or more pressure sensors arranged on a bottom portion of the smart sock to collect pressure data from a bottom of a foot of a user; a wireless transmitter communicatively coupled with the one or more pressure sensors; and a power source coupled with the wireless transmitter.

Clause 2: The smart sock of Clause 1, further comprising one or more ankle sensors arranged on an ankle portion of the smart sock and communicatively coupled with the wireless transmitter.

Clause 3: The smart sock according to any one of Clauses 1-2, wherein the one or more ankle sensors comprise an accelerometer.

Clause 4: The smart sock according to any one of Clauses 1-3, wherein the one or more ankle sensors comprise a gyroscope.

Clause 5: The smart sock according to any one of Clauses 1-4, wherein the one or more ankle sensors comprise a blood pressure sensor.

Clause 6: The smart sock according to any one of Clauses 1-5, wherein the one or more ankle sensors, the wireless transmitter, and the power source are included in a removable component detachably attached to the ankle portion of the smart sock.

Clause 7: The smart sock according to any one of Clauses 1-6, wherein the one or more pressure sensors comprise: two pressure sensors arranged to collect pressure data from a ball of the foot of the user; and one pressure sensor arranged to collect pressure data from a heel of the foot of the user.

Clause 8: A wearable device for a foot of a user, comprising: one or more pressure sensors arranged on a bottom portion of the wearable device to collect pressure data from a bottom of the foot of the user; one or more ankle sensors arranged on an ankle portion of the wearable device; a wireless transmitter communicatively coupled with the one or more pressure sensors and the one or more ankle sensors; and a power source coupled with the wireless transmitter.

Clause 9: The wearable device according to Clause 8, wherein the one or more ankle sensors comprise an accelerometer.

Clause 10: The wearable device according to any one of Clauses 8-9, wherein the one or more ankle sensors comprise a gyroscope.

Clause 11: The wearable device according to any one of Clauses 8-10, wherein the one or more ankle sensors comprise a blood pressure sensor.

Clause 12: The wearable device according to any one of Clauses 8-11, wherein the one or more ankle sensors, the wireless transmitter, and the power source are included in a removable component detachably attached to the ankle portion of the wearable device.

Clause 13: The wearable device according to any one of Clauses 8-12, wherein the one or more pressure sensors comprise: two pressure sensors arranged to collect pressure data from a ball of the foot of the user; and one pressure sensor arranged to collect pressure data from a heel of the foot of the user.

Clause 14: The wearable device according to any one of Clauses 8-13, wherein the wearable device comprises a smart sock.

Clause 15: A method, receiving, from a wearable device on a foot of a user, pressure data for a bottom of the foot of the user; receiving, from the wearable device, ankle sensor data from one or more ankle sensors arranged on an ankle portion of the wearable device; predicting a fall of the user based on the pressure data and the ankle sensor data; and initiating one or more interventions based on the predicted fall.

Clause 16: The method according to Clause 15, wherein the one or more ankle sensors comprise an accelerometer.

Clause 17: The method according to any one of Clauses 15-16, wherein the one or more ankle sensors comprise a gyroscope.

Clause 18: The method according to any one of Clauses 15-17, wherein the one or more ankle sensors comprise a blood pressure sensor.

Clause 19: The method according to any one of Clauses 15-18, wherein the one or more ankle sensors are included in a removable component detachably attached to the ankle portion of the wearable device.

Clause 20: The method according to any one of Clauses 15-19, wherein the wearable device comprises a smart sock.

Clause 21: The method according to any one of Clauses 15-20, wherein predicting the fall comprises: generating a likelihood that the user will fall by processing the pressure data and the ankle sensor data using a first machine learning model; and generating a predicted severity of the predicted fall by processing the pressure data and the ankle sensor data using a second machine learning model.

Clause 22: A system, comprising: a memory comprising computer-executable instructions; and one or more processors configured to execute the computer-executable instructions and cause the processing system to perform a method in accordance with any one of Clauses 15-21.

Clause 23: A system, comprising means for performing a method in accordance with any one of Clauses 15-21.

Clause 24: A non-transitory computer-readable medium comprising computer-executable instructions that, when executed by one or more processors of a processing system, cause the processing system to perform a method in accordance with any one of Clauses 15-21.

Clause 25: A computer program product embodied on a computer-readable storage medium comprising code for performing a method in accordance with any one of Clauses 15-21.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or systems (e.g., the machine learning system 515) or related data available in the cloud. For example, the machine learning system 515 could execute on a computing system in the cloud and train and/or use machine learning models. In such a case, the machine learning system 515 could train models to predict user falls, and store the models at a storage location in the cloud. Doing so allows a user to access this information from any computing system attached to a network connected to the cloud (e.g., the Internet).

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112 (f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A smart sock, comprising:

one or more pressure sensors arranged on a bottom portion of the smart sock to collect pressure data from a bottom of a foot of a user; a stretchable fabric pocket;

a communication link connected to the one or more pressure sensors and terminating with one or more magnets within the stretchable fabric pocket;

and a removable component detachably attached to the smart sock by insertion into the stretchable fabric pocket, the removable component comprising:

a wireless transmitter communicatively coupled with the one or more pressure sensors;

a power source coupled with the wireless transmitter;

and a port that magnetically couples to the communication link within the fabric pocket when the removable component is inserted into the stretchable fabric pocket, wherein:

the pressure data is processed using a machine learning model to predict a fall direction of a future fall for the user, and the predicted fall direction is used to predict a fall severity of the future fall.

2. The smart sock of claim 1, further comprising one or more ankle sensors arranged on an ankle portion of the smart sock and communicatively coupled with the wireless transmitter.

3. The smart sock of claim 2, wherein the one or more ankle sensors comprise an accelerometer.

4. The smart sock of claim 2, wherein the one or more ankle sensors comprise a gyroscope.

5. The smart sock of claim 2, wherein the one or more ankle sensors comprise a blood pressure sensor.

6. The smart sock of claim 2, wherein the one or more ankle sensors are included in the removable component and wherein the stretchable fabric pocket is arranged on the ankle portion of the smart sock.

7. The smart sock of claim 1, wherein the one or more pressure sensors comprise:

two pressure sensors arranged to collect pressure data from a ball of the foot of the user; and one pressure sensor arranged to collect pressure data from a heel of the foot of the user.

8. A wearable device for a foot of a user, comprising:

one or more pressure sensors arranged on a bottom portion of the wearable device to collect pressure data from a bottom of the foot of the user;

stretchable fabric pocket;

a communication link connected to the one or more pressure sensors and terminating with one or more magnets within the stretchable fabric pocket;

and a removable component detachably attached to the wearable device by insertion into the stretchable fabric pocket, the removable component comprising:

one or more ankle sensors; a wireless transmitter communicatively coupled with the one or more pressure sensors and the one or more ankle sensors;

a power source coupled with the wireless transmitter;

and a port that magnetically couples to the communication link within the fabric pocket when the removable component is inserted into the stretchable fabric pocket, wherein:

the pressure data is processed using a machine learning model to predict a fall direction of a future fall for the user, and the predicted fall direction is used to predict a fall severity of the future fall.

9. The wearable device of claim 8, wherein the one or more ankle sensors comprise an accelerometer.

10. The wearable device of claim 8, wherein the one or more ankle sensors comprise a gyroscope.

11. The wearable device of claim 8, wherein the one or more ankle sensors comprise a blood pressure sensor.

12. The wearable device of claim 8, wherein the stretchable fabric pocket is arranged on an ankle portion of the wearable device.

13. The wearable device of claim 8, wherein the one or more pressure sensors comprise:

two pressure sensors arranged to collect pressure data from a ball of the foot of the user; and one pressure sensor arranged to collect pressure data from a heel of the foot of the user.

14. The wearable device of claim 8, wherein the wearable device comprises a smart sock.

15. A method comprising:

receiving, from a wearable device on a foot of a user, pressure data for a bottom of the foot of the user;

receiving, from the wearable device, ankle sensor data from one or more ankle sensors arranged on an ankle portion of the wearable device, wherein:

the wearable device comprises: a stretchable fabric pocket;

a communication link connected to one or more pressure sensors for the bottom of the foot of the user and terminating with one or more magnets within the stretchable fabric pocket; and a removable component detachably attached to the wearable device by insertion into the stretchable fabric pocket, the removable component comprising a port that magnetically couples to the communication link within the fabric pocket when the removable component is inserted into the stretchable fabric pocket;

predicting a future fall of the user based on the pressure data and the ankle sensor data, comprising:

processing the pressure data and the ankle sensor data using a first machine learning model to predict a fall direction of the predicted future fall;

and predicting a fall severity of the future fall based on the fall direction; and initiating one or more interventions based on the future fall.

16. The method of claim 15, wherein the one or more ankle sensors comprise an accelerometer.

17. The method of claim 15, wherein the one or more ankle sensors comprise a gyroscope.

18. The method of claim 15, wherein the one or more ankle sensors comprise a blood pressure sensor.

19. The method of claim 15, wherein the stretchable fabric pocket is arranged on the ankle portion of the wearable device.

20. The method of claim 15, wherein predicting the future fall comprises:

generating a likelihood that the user will fall by processing the pressure data and the ankle sensor data using a second machine learning model; and generating a predicted severity of the predicted fall by processing the pressure data and the ankle sensor data using the first machine learning model.

* * * * *